US009194802B2

(12) United States Patent
Pierre

(10) Patent No.: US 9,194,802 B2
(45) Date of Patent: Nov. 24, 2015

(54) LUMINESCENT PROBES HAVING A PHENANTHRIDINYL ANTENNA, AND METHODS OF USE

(71) Applicant: REGENTS OF THE UNIVERSITY OF MINNESOTA, Minneapolis, MN (US)

(72) Inventor: Valerie Christine Pierre, Vadnais Heights, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 14/022,962

(22) Filed: Sep. 10, 2013

(65) Prior Publication Data

US 2014/0080163 A1 Mar. 20, 2014

Related U.S. Application Data

(60) Provisional application No. 61/701,248, filed on Sep. 14, 2012.

(51) Int. Cl.
*G01N 21/64* (2006.01)
*C09K 11/06* (2006.01)
*C12Q 1/48* (2006.01)
*G01N 33/542* (2006.01)

(52) U.S. Cl.
CPC ............ *G01N 21/6486* (2013.01); *C09K 11/06* (2013.01); *C12Q 1/485* (2013.01); *G01N 33/542* (2013.01); *C09K 2211/1029* (2013.01); *C09K 2211/182* (2013.01); *Y10T 436/147777* (2015.01)

(58) Field of Classification Search
CPC ..................................................... G01N 21/64
USPC ................................................ 435/15, 18, 21
See application file for complete search history.

(56) References Cited

U.S. PATENT DOCUMENTS

| 6,344,360 | B1 | 2/2002 | Colvin et al. |
| 7,517,701 | B2 | 4/2009 | Parker et al. |
| 2008/0312431 | A1 | 12/2008 | Parker et al. |
| 2010/0055665 | A1 | 3/2010 | Parker et al. |
| 2010/0204467 | A1 | 8/2010 | Lamarque et al. |

OTHER PUBLICATIONS

Ian M. Clarkson et al. Experimental assessment of the efficacy of senditised emission in water from a europium ion, following intramolecular excitation by a phenanthridinyl group, New J. Chem, 2000, 24, 377-386.*
Sally E. Plush et al. The effect on the lanthanide luminescence of structurally simple Eu(III) Cyclen complexes upon deprotonation of metal bound water molecules and amide based pendant arms, Dalton Trans., 2010, 39, 3644-3652.*
Mathieu, Celine E, Chiral lanthanide complexes as probe of nucleic acids, Durham E-thesis, 2001.*
Ahmed et al., "Fluorescent Imidazolium-Based Cyclophane for Detection of Guanosine-5'-triphosphate and I⁻ in Aqueous Solution of Physiological pH," *Org. Lett.*, 2011; 13:5476-5479.
Ahmed et al., "A highly selective fluorescent chemosensor for guanosine-5'-triphosphate via excimer formation in aqueous solution of physiological pH," *Chem. Commun.*, Mar. 2012; 48:2662-2664.
Allain et al., "Photophysical approaches to responsive optical probes," *Future Med. Chem.*, 2010; 2:339-350.
Amemiya et al., "Fluorescence-mediated sensing of guanosine derivatives based on multitopic hydrogen bonding," *Chem., Commun.*, 1997; 1027-1028.
Andolina et al., "Luminescence Resonance Energy Transfer in Heterodinuclear Ln$^{III}$ Complexes for Sensing Biologically Relevant Anions," *Eur. J. Inorg. Chem.*, 2011; 2011:154-164.
Barbacid, "ras Genes," *Annu. Rev. Biochem*, 1987; 56:779-827.
Baudoin et al., "Molecular Recognition of Nucleotide Pairs by a Cyclo-Bis-Intercaland-Type Receptor Molecule: A Spectrophotometric and Electrospray Mass Spectrometry Study," *Chem. Eur. J.*, 1999; 5(9):2762-2771.
Bazzicalupi et al., "ATP Recognition and sensing with a phenanthroline-containing polyammonium receptor," *Chem. Commun.*, 2006; 4087-4089.
Berg et al., "A genetically encoded fluorescent reporter of ATP/ADP ratio," *Nat. Methods*, 2009; 6:161-166.
Boaz et al., "The Quenching of Fluorescence. Deviations from the Stern-Volmer Law," *J. Am. Chem. Soc.*, 1950; 72:3435-3443.
Bobba et al., "Chiroptical, ESMS and NMR spectroscopic study of the interaction of enantiopure lanthanide complexes with selected self-complementary dodecamer oligonucleotides," *J. Chem. Soc., Perkin Trans.*, 2001; 2:1729-1737.
Bobba et al., "DNA binding studies of cationic lanthanide complexes bearing a phenanthridinium group," *J. Chem. Soc., Perkin Trans.*, 2001; 2:1738-1741.
Bobba et al., "Highly emissive, nine-coordinate enantiopure lanthanide complexes incorporating tetraazatriphenylenes as probes for DNA," *Chem. Commun.*, 2002; 890-891.
Bobba et al., "Enantiopure lanthanide complexes incorporating a tetraazatriphenylene sensitiser and three naphthyl groups: exciton coupling, intramolecular energy transfer, efficient singlet oxygen formation and perturbation by DNA binding," *Org. Biomol., Chem.*, 2003; 1:1870-1872.
Cacheris et al., "The relationship between thermodynamics and the toxicity of gadolinium complexes," *Magn. Reson. Imaging*, 1990; 8:467-481.
Comby et al., "New Trick for an Old Ligand! The Sensing of Zn(II) Using a Lanthanide Based Ternary Yb(III)-cyclen-8-hydroxyquinoline System as a Dual Emissive Probe for Displacement Assay," *Inorg. Chem.*, 2012; 51:10158-10168.

(Continued)

*Primary Examiner* — Michael G Hartley
*Assistant Examiner* — Jagadishwar Samala
(74) *Attorney, Agent, or Firm* — Mueting, Raasch & Gebhardt, P.A.

(57) ABSTRACT

A molecular probe for the luminescent detection of nucleotides (e.g., adenosine nucleotides) is presented. In certain embodiments, the probe can readily distinguish between the three adenosine nucleotides in buffered aqueous conditions at neutral pH, a need for the direct monitoring of enzymatic reactions converting ATP to ADP or AMP. The probe is most efficient under millimolar concentrations of ATP, which are relevant to intracellular conditions. In preferred embodiments, the long luminescence lifetime of the probe readily enables time-gating experiments.

20 Claims, 20 Drawing Sheets

(56) References Cited

OTHER PUBLICATIONS

Comley, "Kinase Screening and Profiling—spoilt for choice," *Drug Discovery World*, Winter 2006/2007; 7:27-50.
Cudic et al., "Binding of nucleotides in water by phenanthridinium bis(intercaland) receptor molecules," *J. Chem. Soc., Chem. Commun.* 1995; 1073-1075.
Descalzo et al., "Anthrylmethylamine functionalised mesoporous silica-based materials as hybrid fluorescent chemosensors for ATP," *J. Mater. Chem.*, 2005; 15:2721-2731.
Dhaenens et al., "Molecular recognition of nucleosides, nucleotides and anionic planar substrates by a water-soluble Bis-intercaland-type receptor molecule," *J. Chem. Soc., Perkin Trans.*; 1993; 2:1379-1381.
Dickins et al., "Structural, Luminescence, and NMR Studies of the Reversible Binding of Acetate, Lactate, Citrate, and Selected Amino Acids to Chiral Diaqua Ytterbium, Gadolinium, and Europium Complexes," *J. Am. Chem. Soc.*, 2002; 124:12697-12705.
Garber, "The second wave in kinase cancer drugs," *Nat. Biotech*, 2006; 24:127-130.
Hosseini et al., "Multiple molecular recognition and catalysis. A multifunctional anion receptor bearing an anion binding site, an intercalating group, and a catalytic site for nucleotide binding and hydrolysis," *J. Am. Chem. Soc.*, 1990; 112:3896-3904.
Huang et al., "Optimizing the Sensitivity of Photoluminescent Probes Using Time-Resolved Spectroscopy: A Molecular Beacon Case Study," *Anal. Chem.*, 2012; 84:8075-8082.
Imming et al., "Drugs, their targets and the nature and number of drug targets," *Nat. Rev. Drug Discov.*, 2006; 5:821-834.
Kanekiyo et al., "Fluorescence detection of ATP based on the ATP-mediated aggregation of pyrene-appended boronic acid on a polycation," *Chem. Commun.*, 2004; 1006-1007.
Keizer, "Nonlinear fluorescence quenching and the origin of positive curvature in Stern-Volmer plots," *J. Am. Chem. Soc.*, 1983; 105:1494-1498.
Kim et al., "A fluorescent cavitand for the recognition of GTP," *Tetrahedron Lett.*, 2005; 46:6617-6620.
Kotova et al., "Sensing of biologically relevant d-metal ions using a Eu(III)-cyclen based luminescent displacement assay in aqueous pH 7.4 buffered solution," *Chem. Commun.*, 2011; 47:6810-6812.
Kwon et al., "Fluorescent GTP-Sensing in Aqueous Solution of Physiological pH," *J. Am. Chem. Soc.*, 2004; 126:8892-8893.
Li et al., "A Sensitive Colorimetric and Fluorescent Probe Based on a Polythiophene Derivative for the Detection of ATP," *Angew. Chem., Int. Ed. Engl.*, 2005; 44:6371-9-6374.
Lippert et al., "Lanthanide-based luminescent probes for selective time-gated detection of hydrogen peroxide in water and in living cells," *Chem. Commun.*, 2010; 46:7510-7512.
Massue et al., "Selective mono N-alkylations of cyclen in one step syntheses," *Tetrahedron Lett.*, 2007; 48:8052-8055.
McCleskey et al., "Differential Receptors Create Patterns Diagnostic for ATP and GTP," *J. Am. Chem. Soc.*, 2003; 125:1114-1115.
McMahon et al., "Selective Detection of the Reduced Form of Glutathione (GSH) over the Oxidized (GSSG) Form Using a Combination of Glutathione Reductase and a Tb(III)-Cyclen Maleimide Based Lanthanide Luminescent 'Switch on' Assay," *J. Am. Chem. Soc.*, 2012; 134(26):10725-10728.
Miao et al., "Determination of adenosine disodium triphosphate (ATP) using norfloxacin—$Tb^{3+}$ as a fluorescence probe by spectrofluorimetry," *J. Lumin.*, 2006; 116:67-72.
Moore et al., "Concentration-Independent pH Detection with a Luminescent Dimetallic Eu(III)-Based Probe," *J. Am. Chem. Soc.* 2012; 134:17372-17375.
Moro et al., "An ATP fluorescent chemosensor based on a Zn(II)-complexed dipicolylamine receptor coupled with a naphthalimide chromophore," *Chem., Commun.*, 2010; 46:1085-1087.
Morrison et al., "A kinetic method for determining dissociation constants for metal complexes of adenosine 5'-triphosphate and adenosine 5'-diphosphate," *Biochemistry*, 1980; 19:3127-3131.
Naviglio et al., "Protein kinase A as a biological target in cancer therapy," *Expert Opin. Ther. Targets*, 2009; 13:83-92.
Neelakandan et al., "Synthesis of a Novel Cyclic Donor-Acceptor Conjugate for Selective Recognition of ATP," *Org. Lett.*, 2005; 7:5765-5768.
Neelakandan et al., "A Supramolecular ON-OFF-ON Fluorescence Assay for Selective Recognition of GTP," *J. Am. Chem. Soc.*, 2006; 128:11334-11335.
New et al., "Development of responsive lanthanide probes for cellular applications," *Curr. Opin. Chem. Biol.*, 2010; 14:238-246.
Ojida et al., "Efficient fluorescent ATP-sensing based on coordination chemistry under aqueous neutral conditions," *Tetrahedron Lett.*, 2002; 43:6193-6195.
Ojida et al., "Design of Dual-Emission Chemosensors for Ratiometric Detection of ATP Derivatives," *Chem.-Asian J.*, 2006; 1:555-563.
Ojida et al., "Bis(Dpa-$Zn^{II}$) Appended Xanthone: Excitation Ratiometric Chemosensor for Phosphate Anions," *Angew. Chem., Int. Ed. Engl.*, 2006; 45:5518-5521.
Ojida et al., "Turn-On Fluorescence Sensing of Nucleoside Polyphosphates Using a Xanthene-Based Zn(II) Complex Chemosensor," *J. Am. Chem. Soc.*, 2008; 130:12095-12101.
Overington et al., "How many drug targets are there?," *Nat. Rev. Drug Discov.*, 2006; 5:993-996.
Page et al., "Sensitive and selective time-gated luminescence detection of hydroxyl radical in water," *Chem. Commun.*, 2010; 46:2423-2425.
Pershagen et al., "Luminescent Lanthanide Complexes with Analyte-Triggered Antenna Formation," *J. Am. Chem. Soc.*, 2012; 134:9832-9835.
Pivovarenko et al., "Fluorometric detection of adenosine triphosphate with 3-hydroxy-4'-(dimethylamino)flavone in aqueous solutions.," *J. Fluoresc.*, 2006; 16:9-15.
Ramya et al., "Highly Luminescent and Thermally Stable Lanthanide Coordination Polymers Designed from 4-(Dipyridin-2-yl)aminobenzoate: Efficient Energy Transfer from $Tb^{3+}$ to $Eu^{3+}$ in a Mixed Lanthanide Coordination Compound," *Inorg. Chem.*, 2012;51:8818-8826.
Rodrigues et al., "$Tb^{3+} \rightarrow Eu^{3+}$ Energy Transfer in Mixed-Lanthanide-Organic Frameworks," *J. Phys. Chem. C.*, 2012; 116:19951-19957.
Schaferling et al., "Europium Tetracycline as a Luminescent Probe for Nucleoside Phosphates and Its Application to the Determination of Kinase Activity," *Chem.-Eur. J.*, 2007; 13:4342-4349.
Schneider et al., "Coupling Rational Design with Libraries Leads to the Production of an ATP Selective Chemosensor," *J. Am. Chem., Soc.*, 2000; 122:542-543.
Smolensky et al., "Magnetoluminescent Agents for Dual MRI and Time-Gated Fluorescence Imaging," *Eur. J. Inorg. Chem.*, 2012; 12:2141-2147.
Smolensky et al., "Magnetoluminescent Light-Switches: Dual Modality in DNA Detection," *J. Am. Chem. Soc.*, 2013; 135:8966-8972.
Spangler et al., "Kinetic determination of the GTPase activity of Ras proteins by means of a luminescent terbium complex," *Anal. Bioanal. Chem.*, 2009; 394:989-996.
Swamy et al., "Fluorescent sensing of pyrophosphate and ATP in 100% aqueous solution using a fluorescein derivative and $Mn^{2+}$," *Tetrahedron Lett.*, 2007; 48:8683-8686.
Thibon et al., "Principles of responsive lanthanide-based luminescent probes for cellular imaging," *Anal. Bioanal. Chem.*, May 2009; 394:107-120.
Thibon et al., "A Highly Selective Luminescense Sensor for the Time-Gated Detection of Potassium," *J. Am. Chem. Soc.*, 2009; 131:434-435.
Traut, "Physiological concentrations of purines and pyrimidines," *Mol. Cell. Biochem.*, 1994; 140:1-22.
Wang et al., "Combinatorial Synthesis of Benzimidazolium Dyes and Its Diversity Directed Application toward GTP-Selective Fluorescent Chemosensors," *Am. Chem. Soc.*, 2006; 128:10380-10381.
Wang et al., "A cholic acid-based fluorescent chemosenor for the detection of ATP," *Org. Biomol. Chem.*, 2008; 6:162-168.
Weitz et al., "A ratiometric probe for the selective time-gated luminescence detection of potassium in water," *Chem. Commun.*, 2011; 47:541-543.

(56) References Cited

OTHER PUBLICATIONS

Weitz et al., "A Selective Luminescent Probe for the Direct Time-Gated Detection of Adenosine Triphosphate," *J. Am. Chem. Soc.*, 2012; 134(39):16099-16102.

Weitz et al., "The basis for the molecular recognition and the selective time-gated luminescence detection of ATP and GTP by a lanthanide complex," *Chemical Science*, 2013; 4(10):4052-4060.

Wu et al., "Metallohelical Triangles for Selective Detection of Adenosine Triphosphate in Aqueous Media," *Inorg. Chem.*, 2009; 48:408-410.

Xu et al., "Unique Sandwich Stacking of Pyrene-Adenine-Pyrene for Selective and Ratiometric Fluorescent Sensing of ATP at Physiological pH," *J. Am. Chem. Soc.*, 2009; 131:15528-15533.

Xu et al., "Fluorescent Sensing and Discrimination of ATP and ADP Based on a Unique Sandwich Assembly of Pyrene-Adenine-Pyrene," *Chem.-Asian J.*, 2011; 6(8):2114-2122.

Yao et al., "A simple approach for the discrimination of nucleotides based on a water-soluble polythiophene derivative," *Chem. Commun.*, 2009; 4696-4698.

Ye et al., "Development of a Terbium Complex-Based Luminescent Probe for Imaging Endogenous Hydrogen Peroxide Generation in Plant Tissues," *Anal. Chem.*, 2011; 83:4163-4169.

Zeglis et al., "A Mismatch-Selective Bifunctional Rhodium-Oregon Green Conjugate: A Fluorescent Probe for Mismatched DNA," *J. Am. Chem. Soc.*, 2006; 128:5654-5655.

Zhang et al., "A Simple Statistical Parameter for Use in Evaluation and Validation of High Throughput Screening Assays," *J. Biomol. Screen.*, 1999; 4:67-73.

\* cited by examiner

LUMINESCENT PROBES HAVING A PHENANTHRIDINYL ANTENNA, AND METHODS OF USE

This application claims the benefit of U.S. Provisional Application No. 61/701,248, filed Sep. 14, 2012, which is herein incorporated by reference in its entirety.

GOVERNMENT FUNDING

This invention was made with government support under CHE-1151665 awarded by the National Science Foundation. The government has certain rights in the invention.

BACKGROUND

Kinases currently represent one of the two largest classes of targets for drug discovery. In the field of oncology, the FDA's approval of the first kinase inhibitor, Herceptin, in 1998 started an extensive search for cancer drugs that target cellular signaling pathways. The search for new kinase inhibitors, critical tools in cancer therapy, often begins with the high throughput screening (HTS) of libraries followed by the evaluation of the potency of potential leads and their selectivity for a desired kinase. These studies require the widespread availability of efficient and affordable screens for kinase activity. A recent survey highlighted the most important features coveted by researchers in such a platform (Comley, *Drug Discov World* 2006, Winter 2006 Jul., 27). The survey indicated important features including affordability, non-radioactivity, label-free, antibody-free, generic (i.e., able to screen all classes of kinases), and utility for the study of large protein substrates. In addition, other preferred features included time-resolved or time-gated luminescence detection, and assays that measure the accumulation of ADP as opposed to the phosphorylation of a peptide or the displacement of a biomarker. None of the current commercial assays fulfill all of these needs. Moreover, none can be performed at higher concentrations of ATP, closer to the intracellular concentrations of 1-10 mM needed to study inhibitors of low-affinity kinases.

SUMMARY

In one aspect, the present disclosure provides a luminescent probe having a structure of the formula:

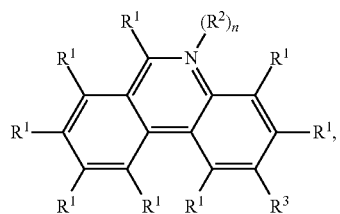

Formula I wherein: each $R^1$ represents hydrogen, an organic group, a halogen, or Z; $R^2$ represents hydrogen, a carbon-bonded organic group, or Z; $R^3$ represents hydrogen, an organic group, or a halogen; wherein for molecules in which one or more of $R^1$, $R^2$, and/or $R^3$ represents an organic group, two or more of $R^1$, $R^2$, and $R^3$ may optionally be joined with one another to form one or more fused rings; n=0 or 1; and Z represents a chelated luminescent Lanthanide (Ln) complex, with the proviso that one $R^1$=Z; or n=1 and $R^2$=Z.

In certain embodiments, the chelated Lanthanide complex includes a polyamino carboxamide chelator such as a 1,4,7,10-tetraazacyclododecane-1,4,7,10-tetraacetamide (DOTAm) chelator. In such embodiments, Z can represent a group of the Formula Z1:

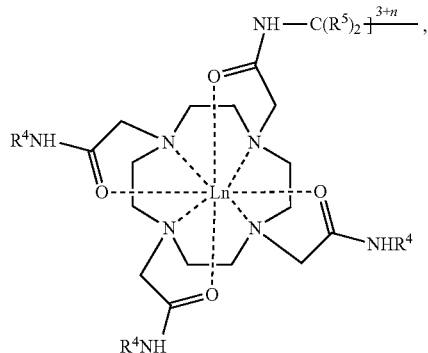

wherein each $R^4$ and $R^5$ independently represent H or an organic group.

In certain embodiments, the chelated Lanthanide complex includes a polyamino carboxamide chelator such as a diethylene triamine pentaacetamide (DTPAm) chelator. In such embodiments, Z can represent a group of the Formula Z2:

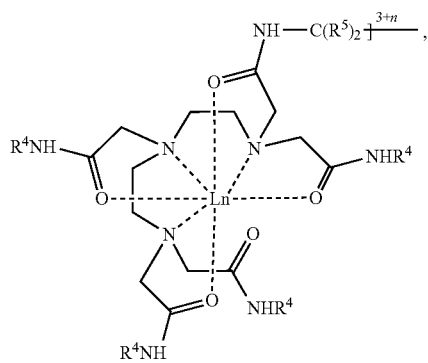

wherein each $R^4$ and $R^5$ independently represent H or an organic group.

In certain embodiments, the luminescent probe has a structure of the formula:

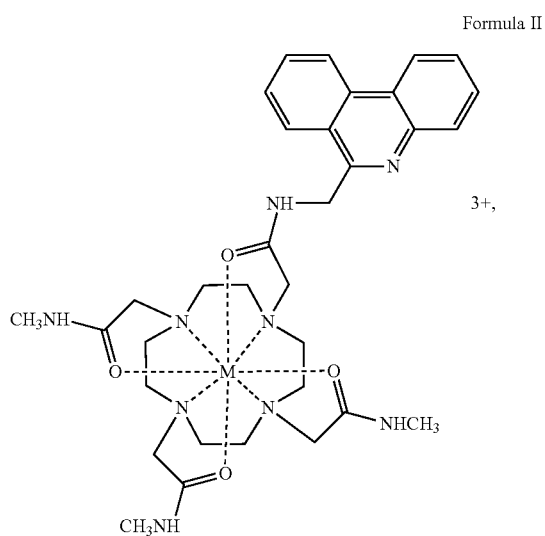

Formula II wherein M represents Tb or Eu.

In certain embodiments, the chelated Lanthanide complex includes a chelator such as a 1,4,7,10-tetraazacyclododecane-1,4,7-triacetic acid-10-acetamide (DOTA) chelator. In such embodiments, Z can represent a group of the Formula Z3:

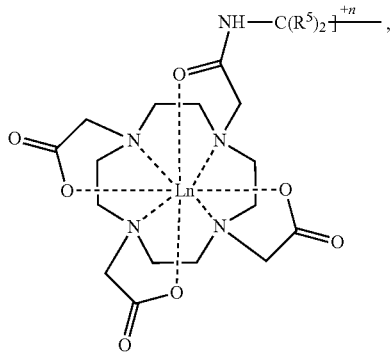

wherein each $R^5$ independently represent H or an organic group.

In certain embodiments, the luminescent probe has a structure of the formula:

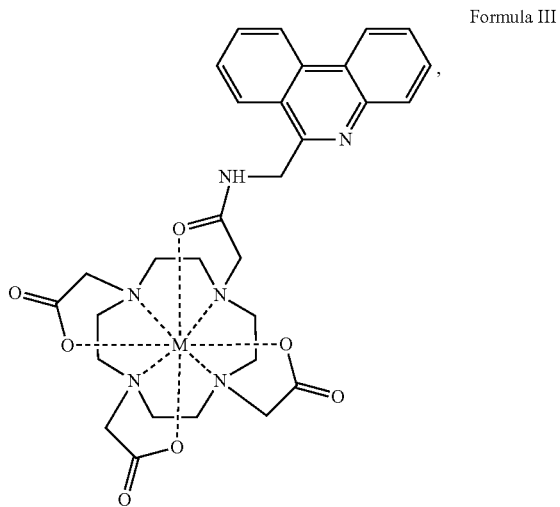

Formula III wherein M represents Tb or Eu.

In another aspect, the present disclosure provides a method of detecting a nucleoside phosphate. The method includes: combining at least one nucleoside phosphate and one or more luminescent probes as disclosed herein in an aqueous medium; and detecting (e.g., using time-delayed detection) a decrease in luminescence at one or more selected wavelengths from the luminescence of the one or more probes at the one or more selected wavelengths in the absence of the at least one nucleoside phosphate, indicating the presence of the at least one nucleoside phosphate. In certain embodiments, the at least one nucleoside phosphate can be a nucleoside monophosphate, a nucleoside diphosphate, a nucleoside triphosphate, or a combination thereof. In certain embodiments, the at least one nucleoside phosphate can be an adenosine phosphate, a guanosine phosphate, a cytosine phosphate, a uridine phosphate, cyclic adenosine monophosphate (cyclic AMP), 6-methyluridine phosphate, 8-bromoguanosine phosphate, thymine phosphate, or a combination thereof.

In certain embodiments, the method can distinguish, by luminescence intensity, adenosine triphosphate (ATP), adenosine diphosphate (ADP), and adenosine monophosphate (AMP) using a Stern-Volmer relationship. In certain embodiments, the method can distinguish, by luminescence intensity, guanosine triphosphate (GTP), guanosine diphosphate (GDP), and guanosine monophosphate (GMP) using a Stern-Volmer relationship. Such methods can be useful for measuring the reaction rates of an enzyme such as a kinase (e.g., an ATPase or a GTPase).

The present disclosure provides a probe that is a small molecule that is luminescent and non-radioactive. Lanthanide complexes such as terbium or europium are preferred as their long luminescence lifetimes, typically in the ms, enable facile time-gated experiments. Time-gating is a favored technique in drug discovery and chemical biology because the delay between the excitation pulse and the emission measurement enables the complete removal of background fluorescence, including those arising from fluorescent drug candidates.

The generic aspect and the need to screen large protein substrate can both be met by designing a probe that binds reversibly and with differential affinity to ATP, ADP, and AMP. If the probe is designed in such a way that binding of the nucleotide affects its luminescence, than the different binding affinity can advantageously be used to monitor conversion from one nucleotide to another. A turn-on response for ATP to ADP conversion can be achieved if both nucleotides quench the luminescence of the probe and if the probe has higher affinity for ATP than ADP. Similarly, turn-on responses for ATP to AMP conversion, GTP to GDP conversion, and GTP to GMP conversion can also be monitored. Lastly, for the probe to be efficient at the high millimolar concentration of ATP typically found intracellularly, the probe must have weak affinity for the nucleotides, in the millimolar range.

In summary, two molecular probes for the detection of nucleotides are disclosed herein. The positively charged [Tb-DOTAm-Phen]$^{3+}$ responds only to purine nucleotides and selectively detects GTP and ATP over GDP/GMP and ADP/AMP, respectively. The neutral Eu-DOTA-Phen complex, on the other hand, is selective for purines over pyrimidines but does not distinguish between tri-, di- and monophosphate nucleotides. Both probes possess long luminescence lifetimes that readily enable time-gated experiments and complete removal of any autofluorescence background. The decrease of the Stern-Volmer constants with temperature is indicative of a static mechanism of quenching in agreement with the formation of a stacked phenanthridine.purine complex. The selectivity of the probes for purines over pyrimidines is due to a higher binding affinity and quenching ability of the more extended purines for the phenanthridine chromophore. The selectivity of the positively charged terbium complex for the tri- over the di- and mono-phosphate nucleotides is due to weak electrostatic interactions with the negatively charged phosphates of ATP and GTP, as evidenced by the lack of any selectivity for ATP/ADP/AMP or GTP/GDP/GMP by the neutral europium complex. Both the selective terbium complex and its non-responsive europium analog can be used concomitantly in the same solution as neither probe affects the response of the other. Simultaneous use of the two chemosensors enables more accurate ratiometric detection of ATP to ADP or GTP to GDP conversion and continuous monitoring of kinase reactions.

DEFINITIONS

The term "comprises" and variations thereof do not have a limiting meaning where these terms appear in the description and claims.

As used herein, "a" "an," "the," "at least one," and "one or more" are used interchangeably.

As used herein, the term "or" is generally employed in the sense as including "and/or" unless the context of the usage clearly indicates otherwise.

Also herein, the recitations of numerical ranges by endpoints include all numbers subsumed within that range (e.g., 1 to 5 includes 1, 1.5, 2, 2.75, 3, 3.80, 4, 5, etc.).

The structures presented herein do not specify any stereoisomers. However, all stereoisomers including distinct optical isomers and mixtures thereof are intended to be included.

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1:
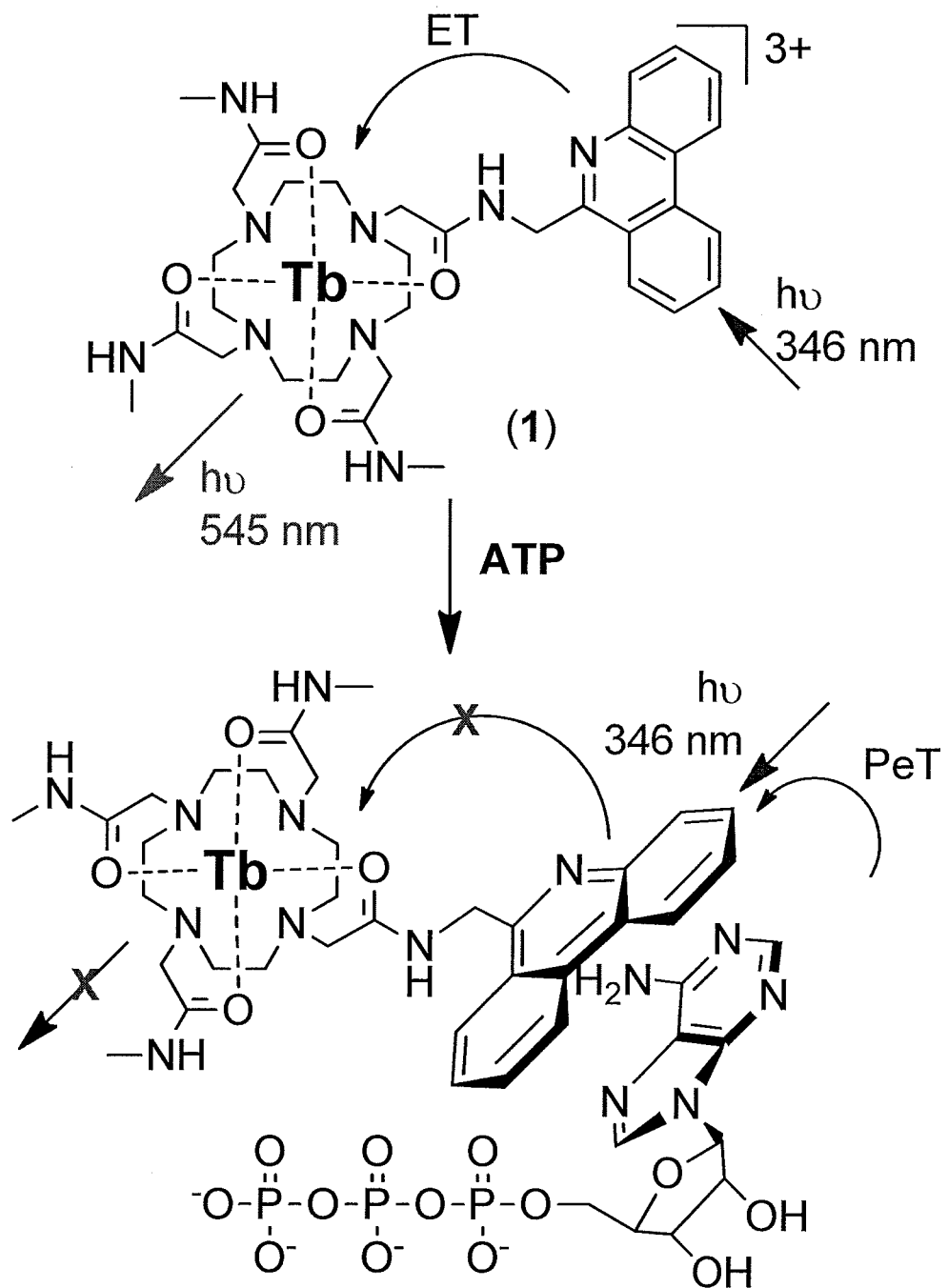
FIG. 1 is a schematic illustration of the chemical structure and mode of action of an exemplary embodiment of a luminescent probe as disclosed herein, ATP sensor Tb-PhenDOTAm (1). In the absence of the nucleotide, excitation of the phenanthridine, followed by energy transfer to the lanthanide enables bright luminescence centered at 545 nm. Stacking of the adenosine on the phenanthridine favors photoelectron transfer (PeT) quenching of the antenna and, consequentially, also that of the Tb luminescence.

Mechanistic and kinetic studies of enzymatic reactions and the regulation of the activity of these enzymes constitute an important part of biochemical and medicinal chemistry research. Enzymes that utilize the nucleotides ATP and GTP represent a substantial portion of clinical targets (Imming et al., *Nat. Rev. Drug Discov.*, 2006, 5, 821-834; and Overington et al. *Nat. Rev. Drug Discov.*, 2006, 5, 993-996). Kinases, ATPases, phosphatases and RNA/DNA polymerases all utilize ATP, with kinases being one of the most promising targets in the fight against cancer and representing one of the two largest classes of targets for drug discovery (Garber, *Nat. Biotech.*, 2006, 24, 127-130). GTP is required for the function of GTPases and their associated GPCRs as well as other guanine nucleotide binding proteins involved in signal transduction pathways. One such example is Ras, a protein for which mutated oncogenes are present in up to 30% of human tumors and which is therefore actively studied (Barbacid, *Annu. Rev. Biochem.*, 1987, 56, 779-827).

Understanding the reaction mechanism of these enzymes, screening and in vitro evaluation of potential inhibitors are crucial first steps in drug discovery. These studies would strongly benefit from readily available luminescent molecular probes that could directly report on the consumption of ATP or GTP without reacting with the analyte. Such probes would not only be appropriate for single point detection as typically performed in high throughput screening, but they would also facilitate continuous monitoring of enzymatic kinetics. Kinetic studies remain one of the most powerful methods to determine, for instance, whether a reaction proceeds via a sequential (random bi-bi or ordered bi-bi) or a ping pong mechanism, or whether any inhibition proceeds via a complete or partial competitive, un-competitive, or non-competitive mechanism.

Given their potential utility, luminescent probes that enable label-free and generic monitoring of enzyme activity have recently received increased attention. A number of absorbance or fluorescence-based chemosensors for ATP and GTP have been proposed. For ATP, see, for example, Schneider et al., *J. Am. Chem. Soc.*, 2000, 122, 542-543; Ojida et al., *Tetrahedron Lett.*, 2002, 43, 6193-6195; Kanekiyo et al., *Chem. Commun.*, 2004, 1006-1007; Neelakandan et al., *Org. Lett.*, 2005, 7, 5765-5768; Li et al., *Angew. Chem., Int. Ed. Engl.*, 2005, 117, 6529-6532; Descalzo et al., *J. Mater. Chem.*, 2005, 15, 2721-2731; Miao et al., *J. Lumin.*, 2006, 116, 67-72; Ojida et al., *Chem. Asian J.* 1, 2006, 1, 555-563; Ojida et al., *Angew. Chem., Int. Ed. Engl.*, 2006, 45, 5518-5521; Bazzicalupi et al., *Chem. Commun.*, 2006, 4087-4089; Pivovarenko et al., *J. Fluoresc.*, 2006, 16, 9-15; Schaferling et al., *Chem.-Eur. J.*, 2007, 13, 4342-4349; Swamy et al., *Tetrahedron Lett.*, 2007, 48, 8683-8686; Wang et al., *Org. Biomol. Chem.*, 2008, 6, 162-168; Wu et al., *Inorg. Chem.*, 2008, 48, 408-410; Ojida et al., *J. Am. Chem. Soc.*, 2008, 130, 12095-12101; Xu et al., *J. Am. Chem. Soc.*, 2009, 131, 15528-15533; Yao et al., *Chem. Commun.*, 2009, 4696-4698; Berg et al., *Nat. Methods*, 2009, 6, 161-166; Moro et al., *Chem. Commun.*, 2010, 46, 1085-1087; and Xu et al., *Chem.-Asian J.*, 2011, 6, 2114-2122. For GTP, see, for example, Amemiya et al., *Chem. Commun.*, 1997, 1027-1028; McCleskey et al., *J. Am. Chem. Soc.*, 2003, 125, 1114-1115; Kwon et al., *J. Am. Chem. Soc.*, 2004, 126, 8892-8893; Kim et al., *Tetrahedron Lett.*, 2005, 46, 6617-6620; Wang et al., *J. Am. Chem. Soc.*, 2006, 128, 10380-10381; Neelakandan et al., *J. Am. Chem. Soc.*, 2006, 128, 11334-11335; Spangler et al., *Anal. Bioanal. Chem.*, 2009, 394, 989-996; Ahmed et al., *Org. Lett.*, 2011, 13, 5476-5479; and Ahmed et al., *Chem. Commun.*, 2012, 48, 2662-2664. In most cases, detection of adenine or guanine is performed via the formation of excimers with extended aromatic groups such as anthracene; any selectivity for the phosphate group is achieved most commonly either via coordination to zinc or by interaction with positively charged H-bond donors. Although studies in which the selectivity versus all twelve nucleotides is reported are scarce, one can nonetheless conclude that the majority of these probes do not portray the necessary selectivity and response for a specific nucleotide (i.e. GTP) as needed for rapid screening. Furthermore, none are currently used commercially.

Aside from the phosphorescent probes disclosed herein (see, also, Weitz et al., *J. Am. Chem. Soc.*, 2012, 134, 16099-16102), another drawback of the rationally designed fluorescent probes reported is their very short luminescence lifetimes which is often combined with short emission wavelengths (typically 350-500 nm). These are particularly disadvantageous for high-throughput screening and kinetic studies given the propensity of some substrates to also fluoresce. This problem is most readily and commonly resolved with the use of emitting lanthanide reporters, such as europium and terbium, which are characterized with long luminescence lifetimes, typically between 0.3-1.5 ms, ideal for facile time-gating experiments (Thibon et al., *Anal. Bioanal. Chem.*, 2009, 394, 107-120; New et al., *Curr. Opin. Chem. Biol.*, 2010, 14, 238-246; and Allain et al., *Future Med. Chem.*, 2010, 2, 339-350). In this technique a delay is set between the excitation pulse and the emission measurements, typically ~0.1 ms, which enables complete removal of background autofluorescence. These advantageous properties of luminescent lanthanide complexes are increasingly exploited in the development of chemosensors and molecular probes and are ever more employed in drug discovery. See, for example, Weitz et al., *J. Am. Chem. Soc.*, 2012, 134, 16099-16102; Page et al., *Chem. Commun.*, 2010, 46, 2423-2425; Lippert et al., *Chem. Commun.*, 2010, 46, 7510-7512; Kotova et al., *Chem. Commun.*, 2011, 47, 6810-6812; Weitz et al., *Chem. Commun.*, 2011, 47, 541-543; Ye et al., *Anal. Chem.*, 2011, 83, 4163-4169; McMahon et al., *J. Am. Chem. Soc.*, 2012, 134, 10725-10728; Pershagen et al., *J. Am. Chem. Soc.*, 2012, 134, 9832-9835; Huang et al., *Anal. Chem.*, 2012, 84, 8075-8082; Comby et al., *Inorg. Chem.*, 2012, 51, 10158-10168; and Moore et al., *J. Am. Chem. Soc.*, 2012, 134, 17372-17375.

Figure 19:
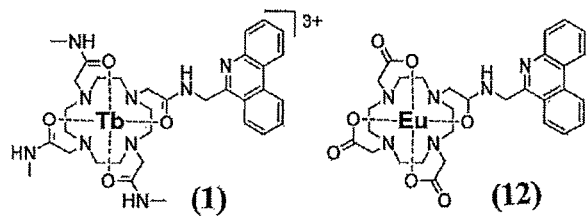
FIG. 19 illustrates chemical structures of [Tb-DOTAm-Phen]$^{3+}$ (1) and Eu-DOTA-Phen (12).
Figure 20:
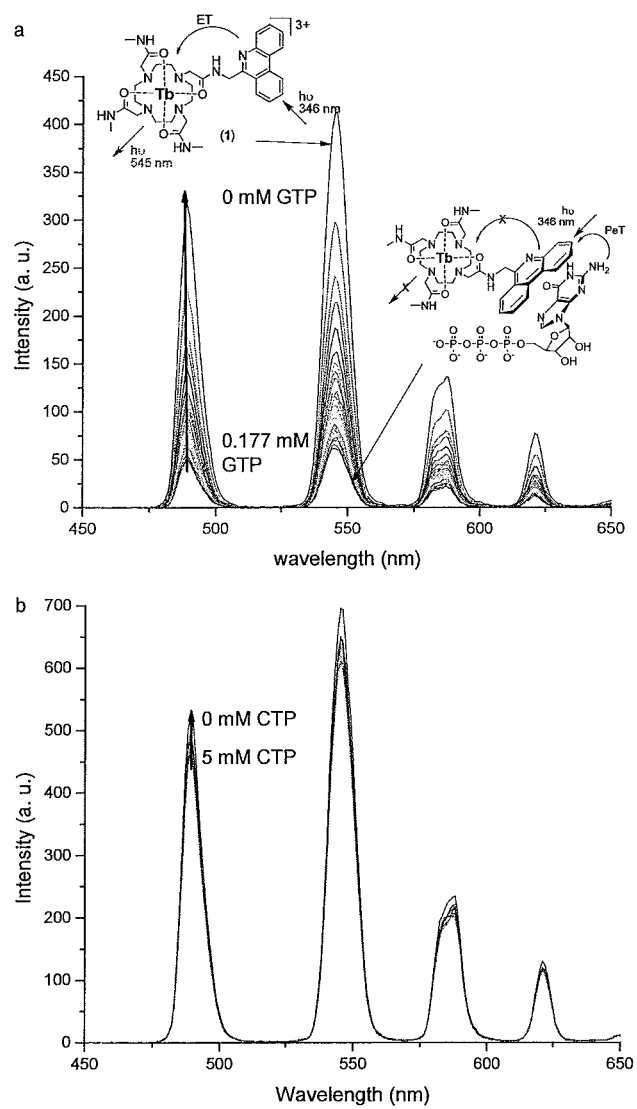
FIG. 20 illustrates a proposed mode of action of GTP sensing with [Tb-DOTAm-Phen]$^{3+}$ and time-delayed luminescence spectra of a) [Tb-DOTAm-Phen]$^{3+}$.GTP and b) [Tb-DOTAm-Phen]$^{3+}$.CTP. Experimental conditions: excitation at 346 nm, time delay=0.1 ms, [Tb-DOTAm-Phen]$^{3+}$=10 μM, water, [Tris]=10 mM, pH 7.0, T=20° C.

Keeping in mind the unmet need of a generic small molecular probe that could directly monitor all classes of enzymatic reactions using ATP regardless of the enzyme's substrate in a non-radioactive and label-free manner by time-gated luminescence detection (Comley, *Drug Discov. World*, 2006, Winter 2006/7, 27-50), a rationally designed terbium complex that could monitor ATP to ADP conversion in a turn-on manner is disclosed herein. See, also, Weitz et al., *J. Am. Chem. Soc.*, 2012, 134, 16099-16102. The probe, [Tb-DOTAm-Phen]$^{3+}$ (1, FIG. 19), is a positively charged macrocyclic lanthanide complex conjugated to a phenanthridine chromophore which behaves as an efficient sensitizing antenna for terbium. In the off-state, excitation of the phenanthridine antenna, followed by intersystem crossing to its triplet state and energy transfer to the excited $^5D$ state of the lanthanide enables phosphorescence of the metal center to its $^7F$ ground state. The complex is thus luminescent in the absence of purine nucleotides. The probe was designed in such a way that weak interactions with a nucleotide would quench the metal-centered emission. Two different interactions were sought to achieve the selectivity. Stacking of the purine base with the phenanthridine chromophore favors photoelectron transfer from the adenine to the antenna which in turn prevents energy transfer from the antenna to the terbium, thereby turning off the probe. Differentiation between the diphosphate and triphosphate nucleotide was subsequently achieved via the positive charge of the probe. The weak electrostatic attraction favors binding to the −4 charged ATP over ADP and AMP (FIG. 20). The steric hindrance surrounding the open coordination site on the lanthanide may prevent direct coordination by the phosphate groups of the nucleotides. This would in turn increase selectivity for ATP over ADP and AMP and maintain a low binding constant such that low affinity kinase enzymes could be studied. Because the probe has a higher affinity for ATP than ADP and because both ATP and ADP quench the probe's luminescence, ATP to ADP conversion causes the lanthanide-centered luminescence to increase.

In one aspect, the present disclosure provides a luminescent probe having a structure of the formula:

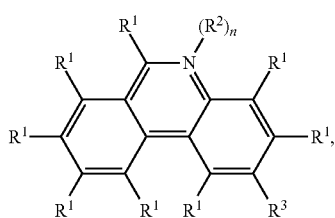

Formula I wherein: each $R^1$ represents hydrogen, an organic group (e.g., a C1-C10 organic group, or in some embodiments a C1-C10 organic moiety), a halogen, or Z; $R^2$ represents hydrogen, a carbon-bonded organic group (e.g., a carbon-bonded C1-C10 organic group, or in some embodiments a carbon-bonded C1-C10 organic moiety), or Z; $R^3$ represents hydrogen, an organic group (e.g., a C1-C10 organic group, or in some embodiments a C1-C10 organic moiety), or a halogen; wherein for molecules in which one or more of $R^1$, $R^2$, and/or $R^3$ represents an organic group, two or more of $R^1$, $R^2$, and $R^3$ may optionally be joined with one another to form one or more fused rings; n=0 or 1; and Z represents a chelated luminescent Lanthanide (Ln) complex, with the proviso that one $R^1$=Z; or n=1 and $R^2$=Z. Optionally, the luminescent probe can further include one or two coordinated water molecules, phosphate, acetate, methanol, or a combination thereof. In certain embodiments, each $R^1$ represents hydrogen or Z; $R^3$ represents hydrogen; n=0; and Z represents a chelated luminescent Terbium (Tb) complex, with the proviso that one $R^1$=Z. The luminescent probe further includes one or more counter ions such as halides, sulfates, carbonates, perchlorate, chlorate, nitrate, acetate, other bases of organic acids, and combinations thereof.

As used herein, the term "organic group" is used for the purpose of this invention to mean a hydrocarbon group that is classified as an aliphatic group, cyclic group, or combination of aliphatic and cyclic groups (e.g., alkaryl and aralkyl groups). In the context of the present invention, suitable organic groups for compounds of this invention are those that do not interfere with the luminescence of the probe. In the context of the present invention, the term "aliphatic group" means a saturated or unsaturated linear or branched hydrocarbon group. This term is used to encompass alkyl, alkenyl, and alkynyl groups, for example. The term "alkyl group" means a saturated linear or branched monovalent hydrocarbon group including, for example, methyl, ethyl, n-propyl, isopropyl, tert-butyl, amyl, heptyl, and the like. The term "alkenyl group" means an unsaturated, linear or branched monovalent hydrocarbon group with one or more olefinically unsaturated groups (i.e., carbon-carbon double bonds), such as a vinyl group. The term "alkynyl group" means an unsaturated, linear or branched monovalent hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polynuclear aromatic hydrocarbon group. The term "heterocyclic group" means a closed ring hydrocarbon in which one or more of the atoms in the ring is an element other than carbon (e.g., nitrogen, oxygen, sulfur, etc.).

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, tert-butyl, and the like.

In certain embodiments, the chelated Lanthanide complex includes a polyamino carboxamide chelator such as a 1,4,7,10-tetraazacyclododecane-1,4,7,10-tetraacetamide (DOTAm) chelator. In such embodiments, Z can represent a group of the Formula Z1:

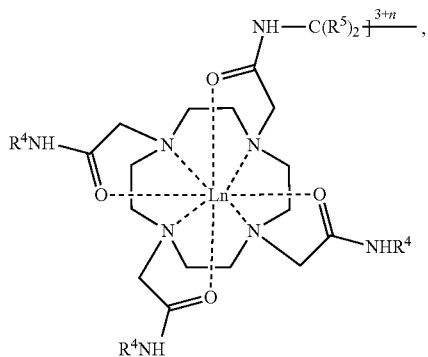

wherein each $R^4$ and $R^5$ independently represent H or an organic group (e.g., a C1-C10 organic group, or in some embodiments a C1-C10 organic moiety). In certain embodiments, each $R^4$ represents a methyl group, and each $R^5$ represents hydrogen.

In certain embodiments, the chelated Lanthanide complex includes a polyamino carboxamide chelator such as a diethylene triamine pentaacetamide (DTPAm) chelator. In such embodiments, Z can represent a group of the Formula Z2:

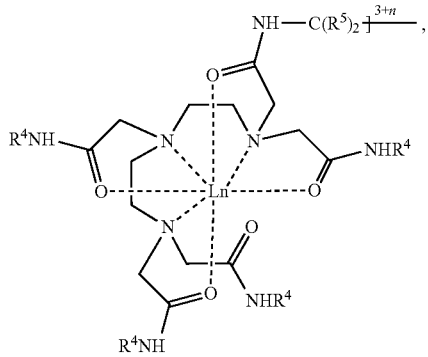

wherein each $R^4$ and $R^5$ independently represent H or an organic group (e.g., a C1-C10 organic group, or in some embodiments a C1-C10 organic moiety). In certain embodiments, each $R^4$ represents a methyl group, and each $R^5$ represents hydrogen.

The Lanthanide can be one or more of the luminescent lanthanides such as La, Ce, Pr, Nd, Pm, Sm, Eu, Tb, Dy, Ho, Er, Tm Yb, Lu, or combinations thereof. In certain embodiments, the Lanthanide can be Tb, Eu, Dy, Tm, Sm, or a combination thereof for emission in the visible range. In other certain embodiments, the Lanthanide can be Yb, Nd, Er, or a combination thereof for emission in the infrared range.

In certain embodiments, the luminescent probe has a structure of the formula:

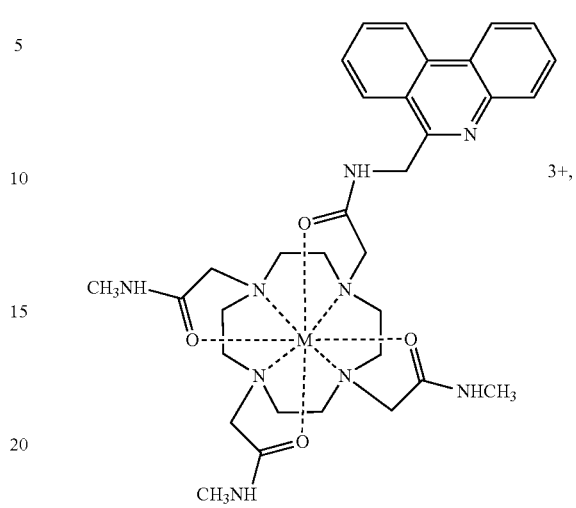

Formula II wherein M represents Tb or Eu.

In certain embodiments, the chelated Lanthanide complex includes a chelator such as a 1,4,7,10-tetraazacyclododecane-1,4,7-triacetic acid-10-acetamide (DOTA) chelator. In such embodiments, Z can represent a group of the Formula Z3:

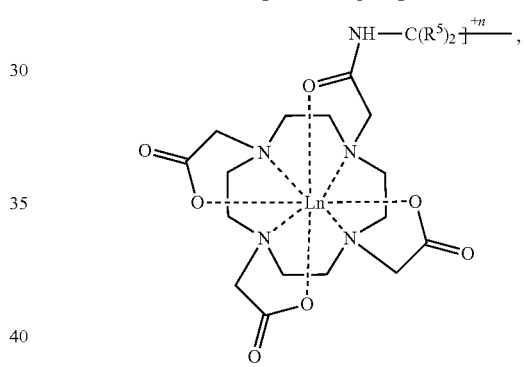

wherein each $R^5$ independently represent H or an organic group (e.g., a C1-C10 organic group, or in some embodiments a C1-C10 organic moiety). In certain embodiments, each $R^5$ represents hydrogen.

In certain embodiments, the luminescent probe has a structure of the formula:

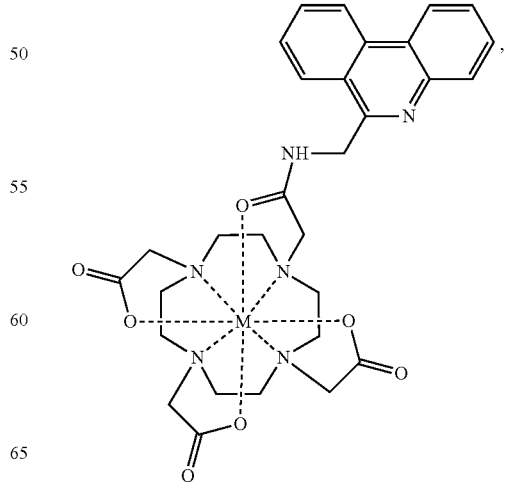

Formula III wherein M represents Tb or Eu.

In some embodiments, the small terbium molecular probe can detect with different binding affinity ATP, ADP, and AMP in buffered aqueous media. In some embodiments, it can fulfill all nine of the user-defined needs. More specifically, the presently disclosed probe takes advantage of three parameters: (1) the need, for practical application, to sensitize terbium luminescence with a nearby antenna whose triplet state is slightly higher in energy than the $^5$D state of the lanthanide (e.g., New et al., *Curr. Opin. Chem. Biol.* 2010, 14, 238; and Thibon et al., *Anal. Bioanal. Chem.* 2009, 394, 107); (2) the ability of adenosine to quench the luminescence of certain chromophores (e.g., New et al., *Curr Opin. Chem. Biol.* 2010, 14, 238; Hosseini et al., *J. Am. Chem. Soc.* 1990, 112, 3896; Dhaenens et al., *J. Chem. Soc., Perkin Trans.* 2 1993, 1379; Cudic et al., *Chem. Commun.* 1995, 1073; Baudoin et al., *Chem. Eur. J* 1999, 5, 2762; Bobba et al., *J. Chem. Soc., Perkin Trans.* 2 2001, 1729; Bobba et al., *J. Chem. Soc., Perkin Trans.* 2 2001, 1738; Bobba et al., *Chem. Commun.* 2002, 890; and Bobba et al., *Org. Biomol. Chem.* 2003, 1, 1870); and (3) differential weak electrostatic interactions between a positively charged metal complex and negatively charged nucleotides.

Figure 3:
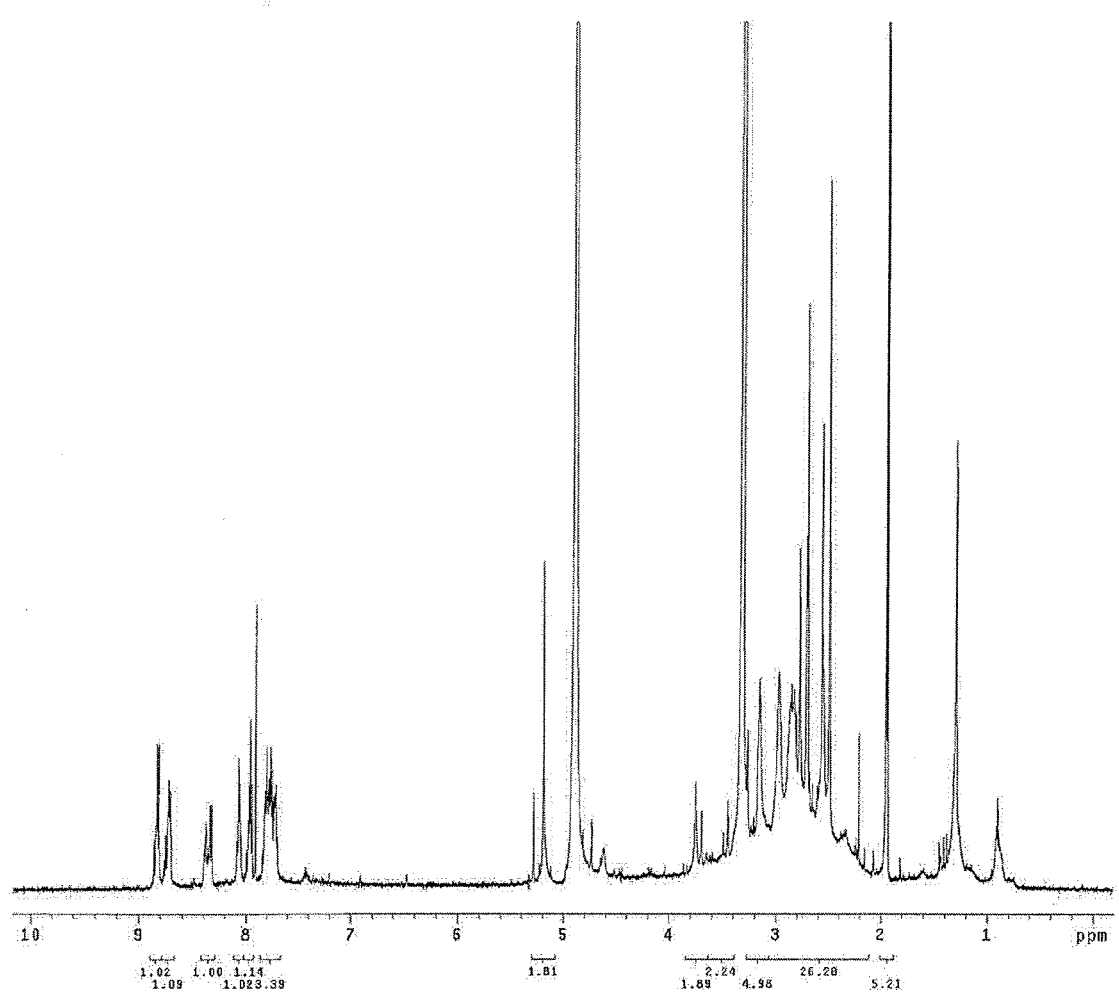
FIG. 3 shows the $^1H$ NMR spectra of the ligand DOTAm-Phen (11, $CD_3OD$, 500 MHz).

The probe, Tb-PhenDOTAm (1), consists of a macrocyclic polyaminocarboxylate terbium complex conjugated to a phenanthridine antenna which is designed as follows (FIG. 1): The macrocyclic DOTA-type chelate gives the complex its high thermodynamic and kinetic stability, thereby preventing any transmetallation with enzymes or peptides (Cacheris et al., *Magn. Reson. Imaging* 1990, 8, 467). The three remaining ligand arms not conjugated to the phenanthridine antenna are converted to amides, thereby giving the complex an overall +3 charge. In the "off" state, that is in the absence of any nucleotide, excitation of the phenanthridine antenna at 346 nm, followed by intersystem crossing from its singlet state to its triplet state and subsequent energy transfer to the terbium $^5$D state yields characteristic terbium phosphorescence with four sharp bands, the most intense centered at 545 nm (FIG. 3).

Figure 2:
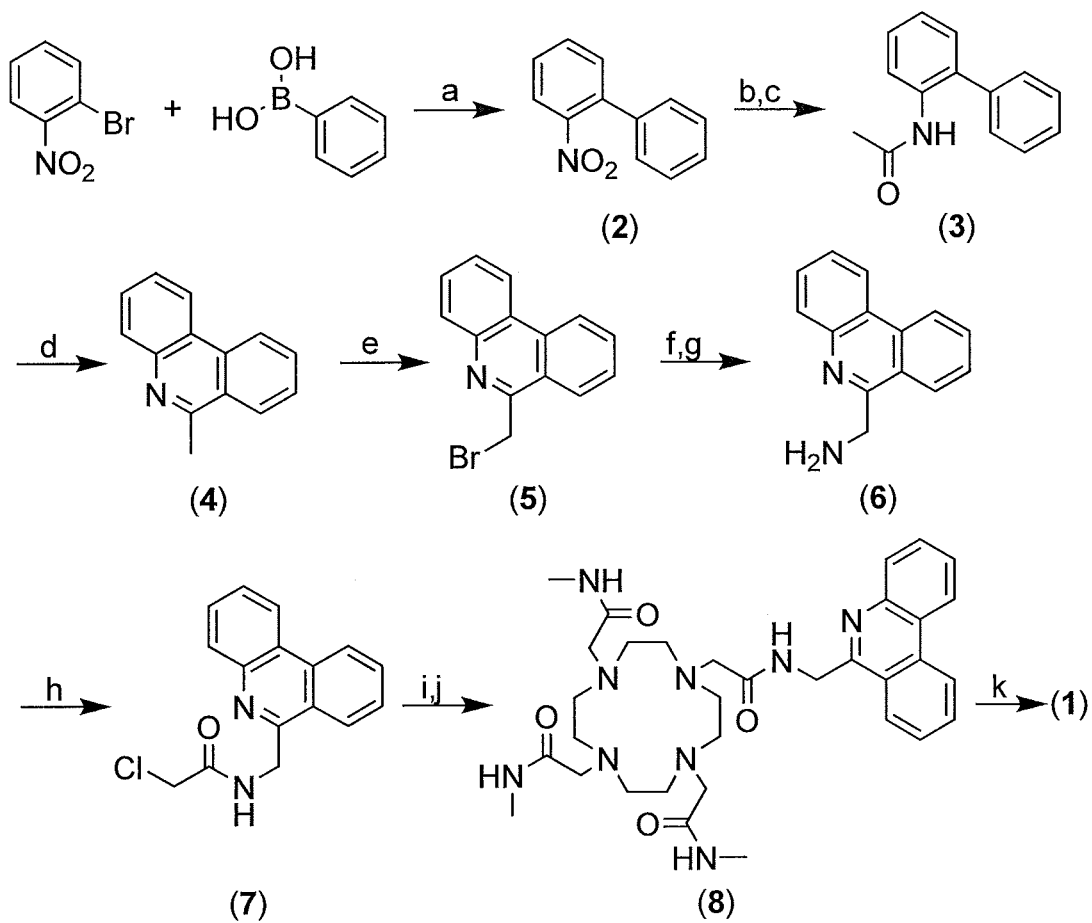
FIG. 2 is a schematic illustration of an exemplary synthesis of Tb-PhenDOTAm (1). Experimental conditions: a) $(PPh_3)_4$ Pd, $Na_2CO_3$, $H_2O$, dimethoxyethane, reflux, 3 hours; b) Pd/C, $H_2$, $CH_3OH$, 12 hours, room temperature; c) $CH_3C(O)Br$, LiOH, $CH_2Cl_2$, 0° C.→room temperature, 2 hours; d) $H_3PO_4$, 150° C., 2.5 hours; e) NBS, hv, room temperature, 45 minutes; f) $NaN_3$, acetone, room temperature, 1 hour; g) Pd/C, $H_2$, $CH_3OH$, 3.5 hours, room temperature; h) $ClCH_2C(O)Cl$, $CH_2Cl_2$, $NEt_3$, room temperature, 2 hours; i) cyclen, $Cs_2CO_3$, $CH_3CN$, DMA, 90° C., 4 hours; j) 2-chloro-N-methylacetamide, $Cs_2CO_3$, $CH_3CN$, 80° C., 34 hours; k) $TbCl_3$, LiOH, $H_2O$, 70° C., 17 hours.

The molecular probe Tb-PhenDOTAm (1) was synthesized according to FIG. 2. Suzuki coupling of 2-bromonitrobenze with phenylboronic acid yielded the nitrobiphenyl (2) which was subsequently reduced to an amine and acetylated to the acetamide (3). The amide was subsequently cyclized to 6-methylphenanthridine (4) in the presence of polyphosphoric acid. Bromination under standard radical conditions, followed by reaction with sodium azide and reduction yielded phenanthridyl-6-ylmethanamine (6) which was then conjugated to the macrocycle following standard conditions in two steps. First, reaction with chloroacetyl chloride yielded the chloride (7) which was then conjugated to the cyclen backbone under basic anhydrous conditions. Addition of the remaining three acetamide arms yielded the hygroscopic ligand DOTAm-Phen (8). The lanthanide complex, Tb-PhenDOTAm (1) was formed quantitatively by refluxing the ligand and one equivalent TbCl$_3$ in water at neutral pH.

In another aspect, the present disclosure provides a method of detecting a nucleoside phosphate. The method includes: combining at least one nucleoside phosphate and one or more luminescent probes as disclosed herein in an aqueous medium; and detecting (e.g., using time-delayed detection) a decrease in luminescence at one or more selected wavelengths from the luminescence of the one or more probes at the one or more selected wavelengths in the absence of the at least one nucleoside phosphate, indicating the presence of the at least one nucleoside phosphate. In some embodiments, the concentration of the one or more nucleoside phosphates is 0.01 to 15 mM, and in certain embodiments, the concentration of the one or more nucleoside phosphates is 1 to 10 mM.

In certain embodiments, the concentration of each of the one or more luminescent probes is 0.5 micromolar to 50 micromolar. Optionally, the aqueous medium further includes a buffer; NaCl, KCl, or other salts; ethylene glycol tetraacetic acid (EGTA); a detergent such as those available under the trade designation BRIJ-35 from ICI Americas; ethylenediaminetetraacetic acid (EDTA); or a combination thereof.

In certain embodiments the method of detecting the nucleoside phosphate includes the use of at least two different luminescent probes. For example, the method can include the use of a luminescent probe that includes a Lanthanide complex of the Formula Z1 (e.g., a luminescent probe of the Formula II) and a luminescent probe that includes a Lanthanide complex of the Formula Z3 (e.g., a luminescent probe of the Formula III).

In certain embodiments, the at least one nucleoside phosphate can be a nucleoside monophosphate, a nucleoside diphosphate, a nucleoside triphosphate, or a combination thereof. In certain embodiments, the at least one nucleoside phosphate can be an adenosine phosphate, a guanosine phosphate, a cytosine phosphate, a uridine phosphate, cyclic adenosine monophosphate (cyclic AMP), 6-methyluridine phosphate, 8-bromoguanosine phosphate, thymine phosphate, or a combination thereof.

In certain embodiments, the luminescence can be measured with excitation at 280 nm to 370 nm. In certain embodiments, detecting the decrease in the luminescence of the probe includes time-delayed detection with, for example, a delay of 0.001 milliseconds to 0.6 milliseconds. In certain embodiments, the luminescence can be detected at one or more wavelengths including, for example, wavelengths of 450 to 690 nm, wavelengths of 800 to 1200 nm, or wavelengths of 1500 to 1600 nm.

In certain embodiments, the method can distinguish, by luminescence intensity, adenosine triphosphate (ATP), adenosine diphosphate (ADP), and adenosine monophosphate (AMP) using a Stern-Volmer relationship. In certain embodiments, the method can distinguish, by luminescence intensity, guanosine triphosphate (GTP), guanosine diphosphate (GDP), and guanosine monophosphate (GMP) using a Stern-Volmer relationship. Such methods can be useful for measuring the reaction rates of an enzyme such as a kinase (e.g., an ATPase or a GTPase).

In certain embodiments, the method can be used to measure the reaction rates of an enzyme such as a kinase, a phosphatase, ATPase, GTPase, an RNA polymerase, or a DNA polymerase. In certain embodiments, the enzyme can be a nucleoside-phosphate kinase, a nucleoside-diphosphate kinase, or a combination thereof. In one exemplary embodiment, the enzyme can be an adenosine-phosphate kinase, an adenosine-diphosphate kinase, or a combination thereof. In another exemplary embodiment, the enzyme can be a guanosine-phosphate kinase, a guanosine-diphosphate kinase, or a combination thereof.

In the presence of ATP, stacking of the purine nucleobase on the antenna favors photoelectron transfer (PeT) from the adenosine to the phenanthridine, thereby preventing energy transfer from the antenna to the lanthanide and, consequently, quenching terbium luminescence. All three adenosine nucleotides may quench the probe's luminescence. Differentiation between ATP, ADP, and AMP may be achieved via weak electrostatic interactions between the +3 charged terbium complex and the negatively charged nucleotides. The higher the number of phosphates, the more negative the charge of the nucleotide, and the higher its affinity for the positively charged probe. Although these interactions are weak in water, they may be sufficient to distinguish the three nucleotides at their millimolar intracellular concentrations. See, for example, Hosseini et al., *J. Am. Chem. Soc.* 1990, 112, 3896; Dhaenens et al., *J. Chem. Soc., Perkin Trans.* 2 1993, 1379; Cudic et al., *Chem. Commun.* 1995, 1073; Baudoin et al., *Chem. Eur J.* 1999, 5, 2762; and Zeglis et al., *J. Am. Chem. Soc.* 2006, 128, 5654.

Figure 17:
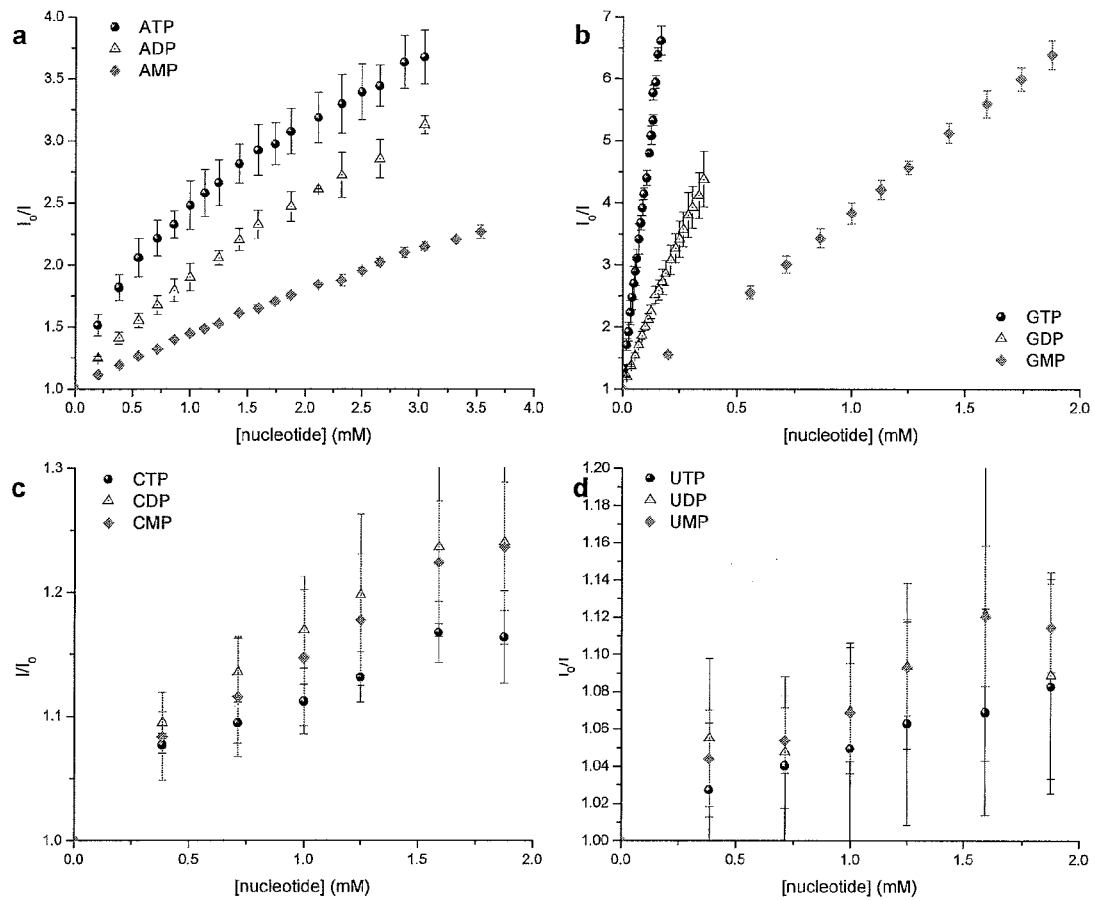
FIG. 17 illustrates Stern-Volmer plots of the time-delayed luminescence quenching of Tb-PhenDOTAm by a) adenosine, b) guanosine, c) cytosine and d) uridine nucleotides. Experimental conditions: excitation at 346 nm, time-delay 0.1 ms, emission slit width=5 nm, excitation slit width=5 nm, [Tb-PhenDOTAm]=10 μM, water, [Tris]=10 mM, pH 7.0, T=20° C.

The response of Tb-PhenDOTAm (1) to the nucleotides ATP, ADP, and AMP in buffered aqueous solution at 20° C. is shown in FIG. 17. A typical time-gated titration of the probe with ATP is shown in FIG. 3. The probe works most efficiently with ATP concentrations between 1-10 mM, concentrations which are within the intracellular range and which are therefore more relevant to drug screening. Moreover, the long luminescence lifetime of the terbium complex readily enables time-delayed experiments, whereby the background luminescence of the sample (enzyme, peptide, fluorescent drugs) can be readily gated out, thereby yielding more accurate measurements, not influenced by the autofluorescence of the system.

Figure 6:
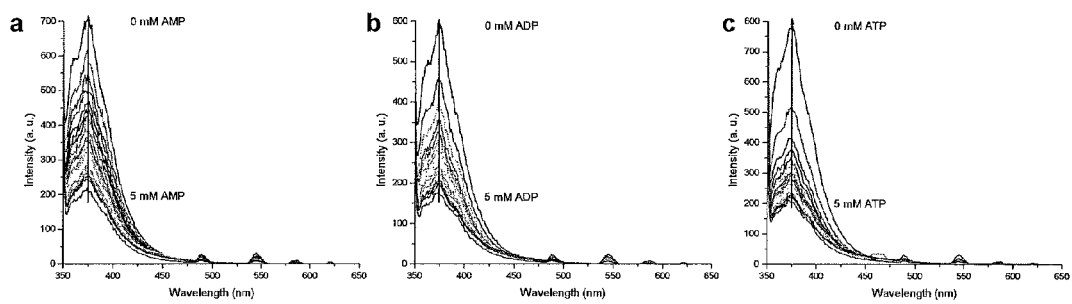
FIG. 6 illustrates fluorescence spectra of a) Tb-PhenDOTAm.AMP, b) Tb-PhenDOTAm.ADP and c) Tb-PhenDOTAm.ATP titrations. Experimental conditions: excitation at 346 nm, emission slit width=5 nm, excitation slit width=5 nm, [Tb-PhenDOTAm]=10 μM, water, [Tris]=10 mM, pH 7.0, T=20° C.
Figure 7:
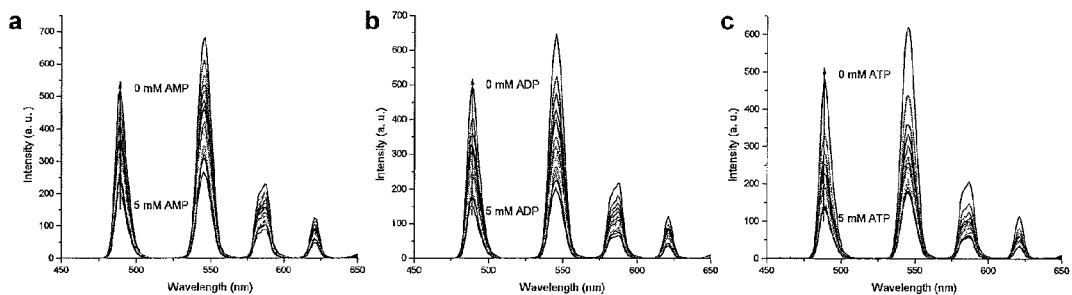
FIG. 7 illustrates time-delayed luminescence spectra of a) Tb-PhenDOTAm.AMP, b) Tb-PhenDOTAm.ADP and c) Tb-PhenDOTAm.ATP titrations. Experimental conditions: excitation at 346 nm, time-delay 0.1 ms, emission slit width=5 nm, excitation slit width=5 nm, [Tb-PhenDOTAm]=10 μM, water, [Tris]=10 mM, pH 7.0, T=20° C.
Figure 8:
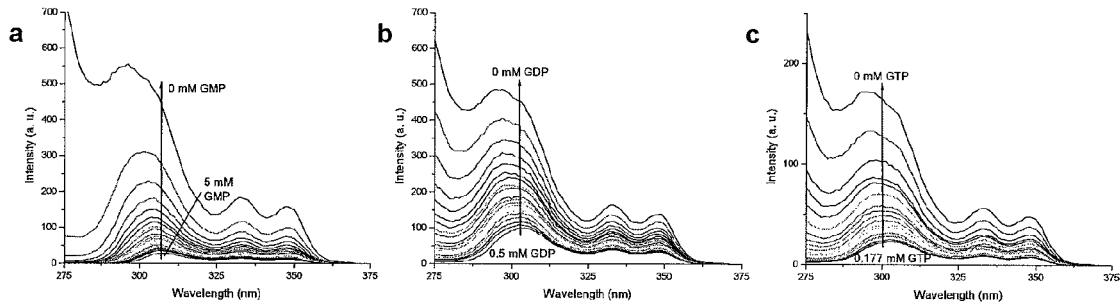
FIG. 8 illustrates time-delayed excitation spectra of a) Tb-PhenDOTAm.GMP, b) Tb-PhenDOTAm.GDP and c) Tb-PhenDOTAm.GTP titrations. Experimental conditions: emission at 545 nm, time-delay 0.1 ms, emission slit width=5 nm, excitation slit width=5 nm, [Tb-PhenDOTAm]=10 μM, water, [Tris]=10 mM, pH 7.0, T=20° C.
Figure 9:
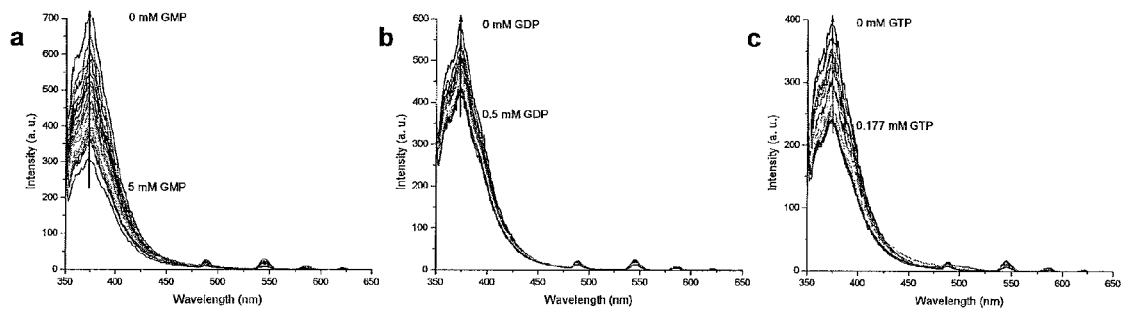
FIG. 9 illustrates fluorescence spectra of a) Tb-PhenDOTAm.GMP, b) Tb-PhenDOTAm.GDP and c) Tb-PhenDOTAm.GTP titrations. Experimental conditions: excitation at 346 nm, emission slit width=5 nm, excitation slit width=5 nm, [Tb-PhenDOTAm]=10 μM, water, [Tris]=10 mM, pH 7.0, T=20° C.
Figure 10:
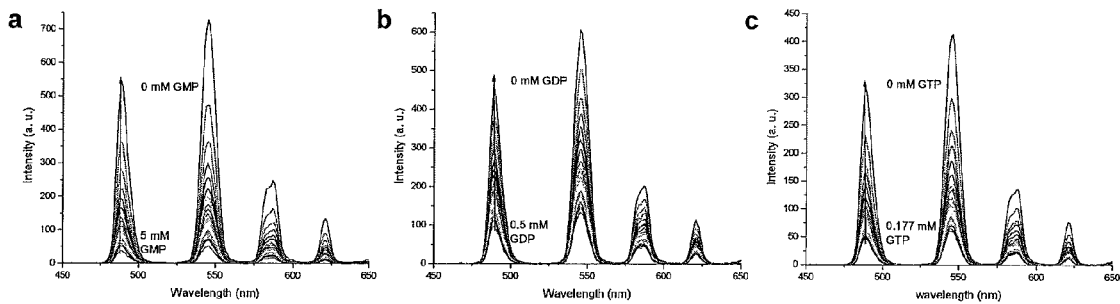
FIG. 10 illustrates time-delayed luminescence spectra of a) Tb-PhenDOTAm.GMP, b) Tb-PhenDOTAm.GDP and c) Tb-PhenDOTAm.GTP titrations. Experimental conditions: excitation at 346 nm, time-delay 0.1 ms, emission slit width=5 nm, excitation slit width=5 nm, [Tb-PhenDOTAm]=10 water, [Tris]=10 mM, pH 7.0, T=20° C.
Figure 11:
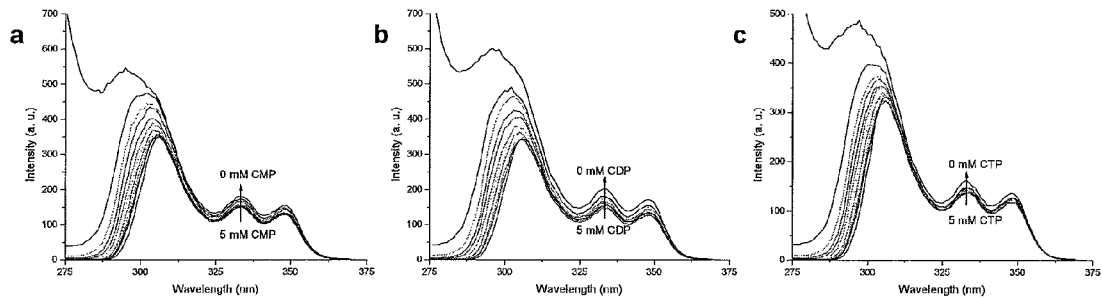
FIG. 11 illustrates time-delayed excitation spectra of a) Tb-PhenDOTAm.CMP, b) Tb-PhenDOTAm.CDP and c) Tb-PhenDOTAm.CTP titrations. Experimental conditions: emission at 545 nm, time-delay 0.1 ms, emission slit width=5 nm, excitation slit width=5 nm, [Tb-PhenDOTAm]=10 μM, water, [Tris]=10 mM, pH 7.0, T=20° C.
Figure 12:
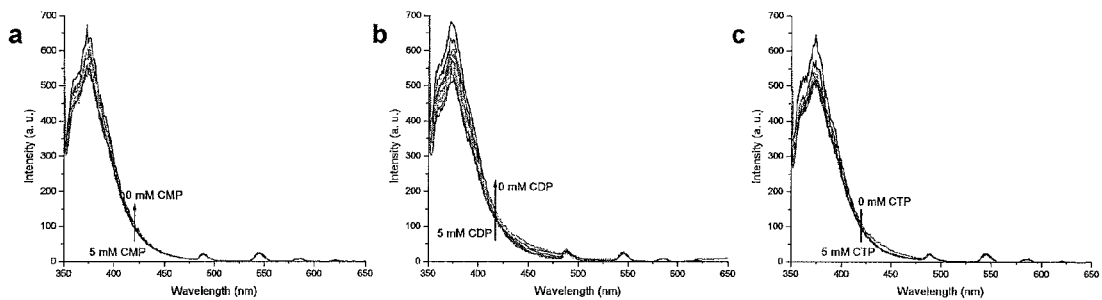
FIG. 12 illustrates fluorescence spectra of a) Tb-PhenDOTAm.CMP, b) Tb-PhenDOTAm.CDP and c) Tb-PhenDOTAm.CTP titrations. Experimental conditions: excitation at 346 nm, emission slit width=5 nm, excitation slit width=5 nm, [Tb-PhenDOTAm]=10 μM, water, [Tris]=10 mM, pH 7.0, T=20° C.
Figure 13:
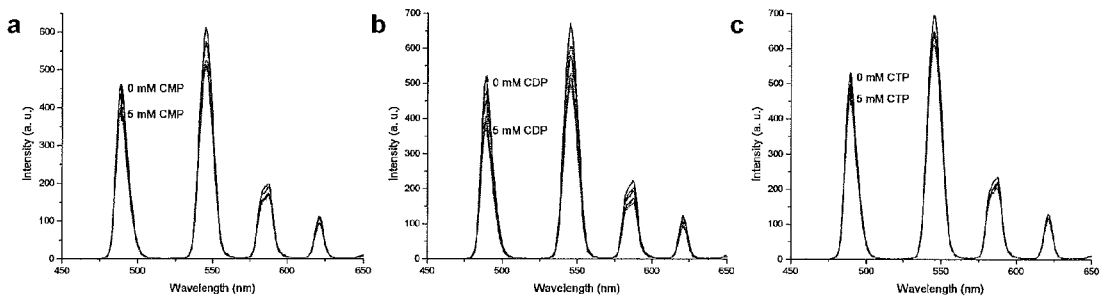
FIG. 13 illustrates time-delayed luminescence spectra of a) Tb-PhenDOTAm.CMP, b) Tb-PhenDOTAm.CDP and c) Tb-PhenDOTAm.CTP titrations. Experimental conditions: excitation at 346 nm, time-delay 0.1 ms, emission slit width=5 nm, excitation slit width=5 nm, [Tb-PhenDOTAm]=10 water, [Tris]=10 mM, pH 7.0, T=20° C.
Figure 14:
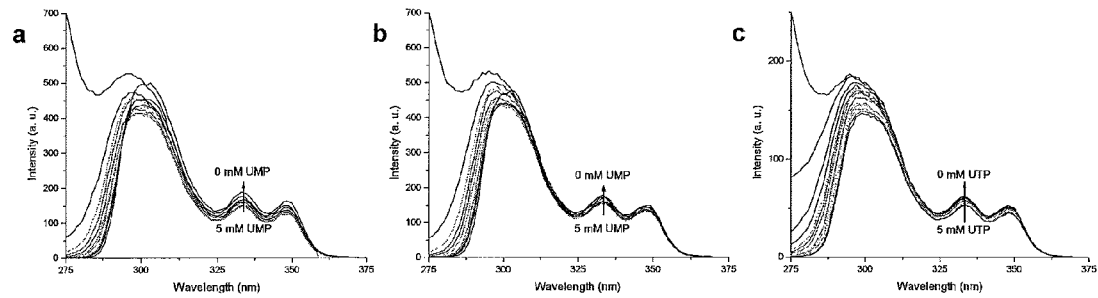
FIG. 14 illustrates time-delayed excitation spectra of a) Tb-PhenDOTAm.UMP, b) Tb-PhenDOTAm.UDP and c) Tb-PhenDOTAm.UTP titrations. Experimental conditions: emission at 545 nm, time-delay 0.1 ms, emission slit width=5 nm, excitation slit width=5 nm, [Tb-PhenDOTAm]=10 μM, water, [Tris]=10 mM, pH 7.0, T=20° C.
Figure 15:
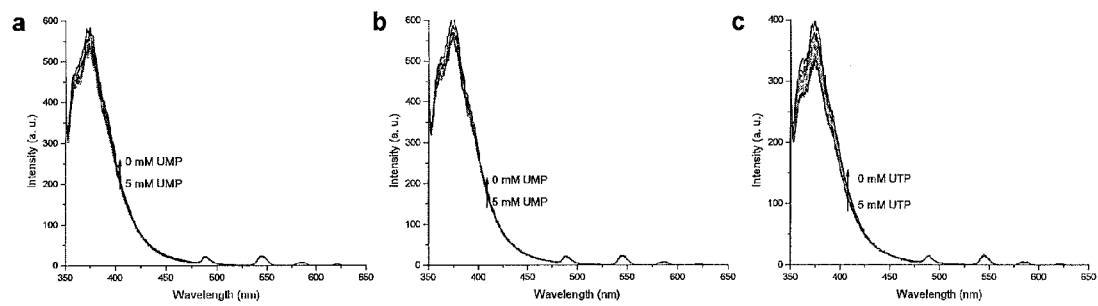
FIG. 15 illustrates fluorescence spectra of a) Tb-PhenDOTAm.UMP, b) Tb-PhenDOTAm.UDP and c) Tb-PhenDOTAm.UTP titrations. Experimental conditions: excitation at 346 nm, emission slit width=5 nm, excitation slit width=5 nm, [Tb-PhenDOTAm]=10 μM, water, [Tris]=10 mM, pH 7.0, T=20° C.
Figure 16:
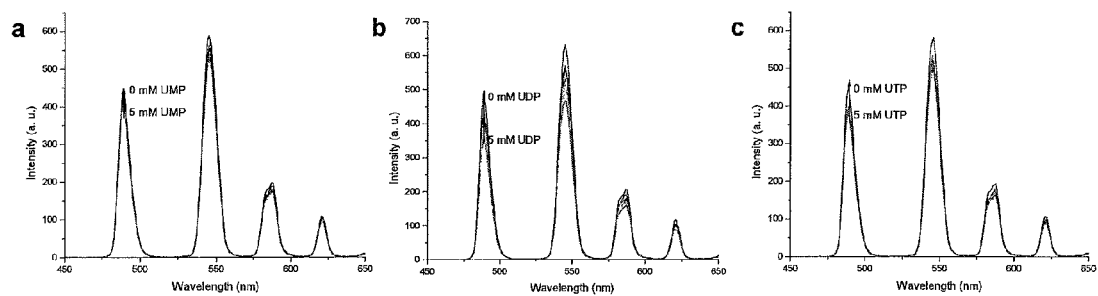
FIG. 16 illustrates time-delayed luminescence spectra of a) Tb-PhenDOTAm.UMP, b) Tb-PhenDOTAm.UDP and c) Tb-PhenDOTAm.UTP titrations. Experimental conditions: excitation at 346 nm, time-delay 0.1 ms, emission slit width=5 nm, excitation slit width=5 nm, [Tb-PhenDOTAm]=10 μM, water, [Tris]=10 mM, pH 7.0, T=20° C.

The Stern-Volmer plot of the time-gated luminescence of the terbium probe in the presence of the three adenosine nucleotides is shown in FIG. 17. Each nucleotide quenches both terbium phosphorescence (FIG. 7) and the antenna's luminescence (FIG. 6) efficiently. The fact that the antenna's luminescence is also quenched strongly suggests that terbium phosphorescence is quenched via a mechanism that involves photoelectron transfer (PeT) from the purine to the phenanthridine (FIG. 1). Importantly, the three nucleotides, ATP, ADP, and AMP, can be readily distinguished and present noticeably different Stern-Volmer constants, $K_{SV}$ (Table 1). At the intracellularly-relevant concentration of 1 mM, ATP quenches 59.7% of Tb-PhenDOTAm's time-gated luminescence. At that same concentration, ADP quenches 47.4% of the probe's phosphorescence, whereas AMP quenches only 31.0%.

The Stern-Volmer relationship observed does not curve upward as the concentration of nucleotide increases. This indicates that quenching is either purely dynamic or purely static in nature, but not both (Keizer, *J. Am. Chem. Soc.* 1983, 105, 1494.). Since quenching involves the adenosine moiety (phosphates and sugars do not quench terbium luminescence), a purely dynamic (collisional) mechanism would have resulted in identical Stern-Volmer constants for each nucleotide. The significantly different Stern-Volmer constants of the linear plots, however, strongly suggests formation of 1:1 complexes between the probe and the nucleotides, likely involving stacking of the purine base on the aromatic antenna. Differentiation between the three nucleotides is likely the result of electrostatic interactions between the positively charged terbium probe and the negatively charged nucleotides: the greater the negative charge of the nucleotide, the higher its Stern-Volmer constant. A similar terbium probe which is instead charged neutral is also efficiently quenched by adenosine nucleotides, but it does not differentiate ATP from ADP and AMP. Electrostatic interactions, albeit weak, have already been used in molecular recognition in water. See, for example, Hosseini et al., *J. Am. Chem. Soc.* 1990, 112, 3896; Dhaenens et al., *J. Chem. Soc., Perkin Trans.* 2 1993, 1379; Cudic et al., *Chem. Commun.* 1995, 1073; Baudoin et al., *Chem. Eur. J.* 1999, 5, 2762; and Zeglis et al., *J. Am. Chem. Soc.* 2006, 128, 5654.

TABLE 1

Stern-Volmer constants of Tb-PhenDOTAm with nucleotides.[a]

| | $K_{SV}$ |
|---|---|
| Adenosines | |
| ATP | 1.28 ± 0.05 |
| ADP | 0.85 ± 0.02 |
| AMP | 0.397 ± 0.005 |
| Guanosines | |
| GTP | 33.1 ± 0.1 |
| GDP | 9.84 ± 0.05 |
| GMP | 2.84 ± 0.01 |
| Cytosines | |
| CTP | 0.103 ± 0.007 |
| CDP | 0.149 ± 0.009 |
| CMP | 0.139 ± 0.006 |
| Uridines | |
| UTP | 0.047 ± 0.002 |
| UDP | 0.065 ± 0.007 |
| UMP | 0.070 ± 0.004 |

[a]Experimental conditions: excitation at 346 nm, emission integrated from 450 nm-650 nm, time-delay 0.1 ms, [Tb-PhenDOTAm] = 10 µM, water, [Tris] = 10 mM, pH 7.0, T = 20° C., error represents standard deviation with n = 3.

Figure 18:
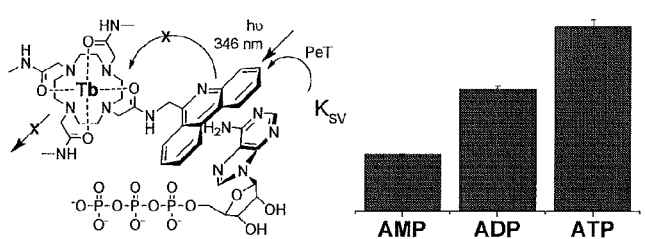
FIG. 18 is a schematic diagram illustrating that Tb-PhenDOTAm (1) can be an efficient molecular probe for the time-gated molecular detection of adenosine nucleotides.

In summary and as illustrated in FIG. 18, Tb-PhenDOTAm (1) is an efficient molecular probe for the time-gated molecular detection of adenosine nucleotides. Its ability to readily distinguish ATP from ADP and AMP under physiologically-relevant conditions renders it an attractive candidate for direct monitoring of enzymatic reactions involving, for example, ATP hydrolysis such as those of kinases and ATPases, and those involving the formation of ATP.

Figure 21:
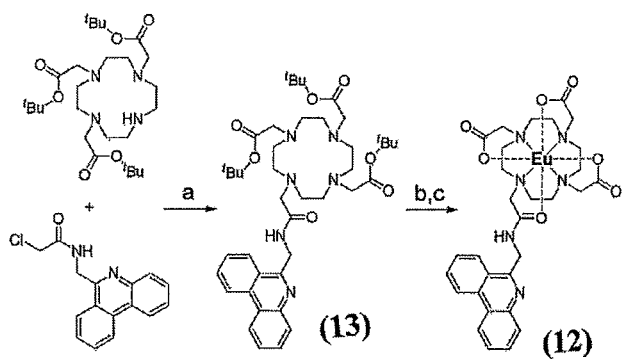
FIG. 21 illustrates an exemplary synthesis of Eu-DOTA-Phen (12). Reagents and conditions: (a) $K_2CO_3$, $CH_3CN$/DMF, 80° C., 27 hours; (b) TFA, $CH_2Cl_2$, 0 to 25° C., 65 hours; (c) $EuCl_3$, LiOH, $H_2O$, 100° C., 19 hours.

In further embodiments, experimental results supporting the molecular probes disclosed herein can extend their application to the detection of GTP to GDP or GMP conversion. The design of luminescent probes for ATP and GTP can be divided into three parts: 1) an extended aromatic antenna which favors hydrophobic stacking with purine nucleobases; this in turn enables PeT from adenine or guanine to the phenanthridine with subsequent quenching of the probe's metal-centered emission; 2) a sterically hindered open coordination site on the lanthanide which prevents direct coordination of the phosphate groups, thereby increasing the selectivity for triphosphate over diphosphate and monophosphates; and 3) peripheral amide arms that bestow a positive charge to the terbium complex, thereby enabling weak electrostatic attractions with, and differentiation of the nucleotides. Each of these parameters were investigated with the parent [Tb-DOTAm-Phen]$^{3+}$ (1) and its neutral analog, Eu-DOTA-Phen (12). The latter was synthesized in three steps from previously reported precursors according to FIG. 21 (see Examples for details).

The two complexes [Tb-DOTAm-Phen]$^{3+}$ and Eu-DOTA-Phen were designed such that recognition of ATP and GTP would involve hydrophobic stacking of the purine nucleobases with the extended aromatic chromophore of the molecular probes. This interaction would in turn favor PeT from either purine to the phenanthridine, thereby preventing further energy transfer to the emitting lanthanide ion. This design was based on previous studies with similar complexes bearing an intercalating antenna which demonstrated that DNA intercalation effectively quenched the lanthanide's luminescence. See, for example, Bobba et al., *Org. Biomol. Chem.*, 2003, 1, 1870-1872; Bobba et al., *J. Chem. Soc., Perkin Trans.* 2, 2001, 1729-1737; Bobba et al., *Chem. Commun.*, 2002, 890-891; Bobba et al., *J. Chem. Soc., Perkin*

Trans. 2, 2001, 1738-1741; and Smolensky et al., submitted for publication. In this mechanism both the short-lived fluorescence of the antenna and the long-lived phosphorescence of the lanthanide are quenched. In support of this mode of molecular recognition, every fluorescent and time-gated luminescent spectrum of adenosine and guanosine nucleotides with (1) and (12) show near complete quenching of both the antenna's and the lanthanide's luminescence (FIG. 20a).

Figure 22:
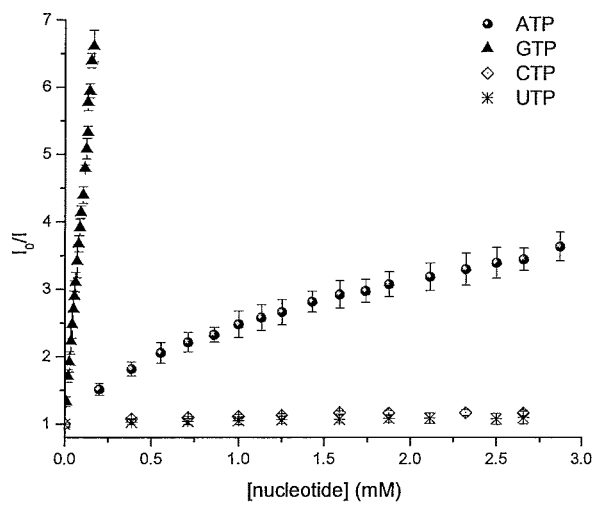
FIG. 22 illustrates a Stern-Volmer plot of the time-delayed luminescence of [Tb-DOTAm-Phen]$^{3+}$ (1) by the triphosphate nucleotides ATP (filled circles), GTP (filled triangles), CTP (open diamonds) and UTP (stars). Experimental conditions: excitation at 346 nm, emission integrated from 450 to 650 nm, time-delay=0.1 ms, [Tb-DOTAm-Phen]$^{3+}$=10 μM, water, [Tris]=10 mM, pH 7.0, T=20° C., error bars represent standard deviation, n=3.
Figure 23:
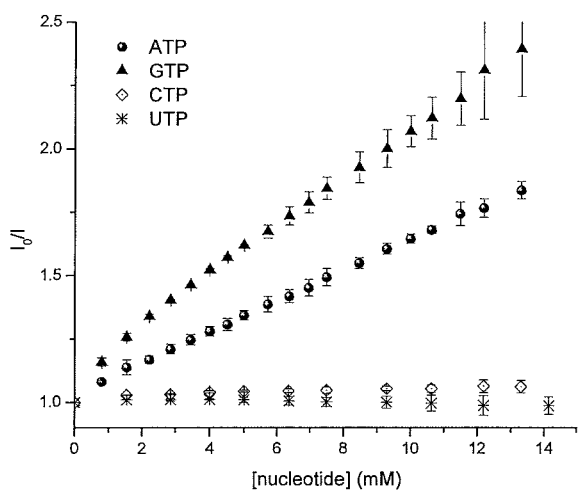
FIG. 23 illustrates a Stern-Volmer plot of the time-delayed luminescence of Eu-DOTA-Phen (12) by the triphosphate nucleotides ATP (filled circles), GTP (closed triangles), CTP (open diamonds) and UTP (stars). Experimental conditions: excitation at 346 nm, emission integrated from 550 to 750 nm, time-delay=0.1 ms, Eu-DOTA-Phen=10 μM, water, [Tris]=10 mM, pH 7.0, T=20° C., error bars represent standard deviation, n=3.
Figure 24:
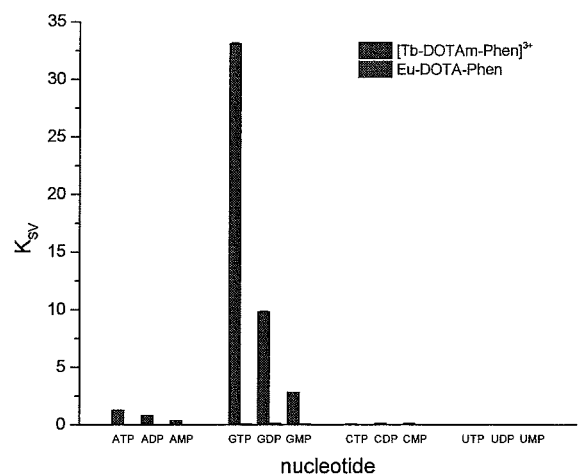
FIG. 24 is a graphical representation of Stern-Volmer constants of [Tb-DOTAm-Phen]$^{3+}$ (gray) and Eu-DOTA-Phen (black) with nucleotides. Error bars represent standard deviation, n=3.

Significantly, whereas the luminescence of both probes is effectively quenched by adenosine and guanosine nucleotides, neither probe can report on the presence of cytosines or uridines (FIGS. 20, 22 and 23). The observed quenching and the calculated Stern-Volmer constants (Table 2 and FIG. 24) are apparent binding constants; they are a function of both the affinity of the probe for its substrate and the ability of the substrate to quench the luminescence of the probe. The higher $K_{SV}$ of both [Tb-DOTAm-Phen]$^{3+}$ and Eu-DOTA-Phen for GTP and ATP (FIGS. 22 and 23, respectively) are thus a combination of the higher affinity of phenanthridine for the more extended aromatics of purines and of the higher energy level of the HOMO of guanine, and to a lesser extent adenine, as needed for efficient PeT quenching of the excited singlet state of the phenanthridine antenna. The inability of pyrimidines to quench the phenanthridine antenna and the emitting lanthanide is thus likely the result of their lower HOMOs.

TABLE 2

Stern-Volmer constants ($K_{sv}$) of [Tb-DOTAm-Phen]$^{3+}$ (1) and Eu-DOTA-Phen (12) with nucleotides.[a]

| Nucleotides | [Tb-DOTAm-Phen]$^{3+}$ | Eu-DOTA-Phen |
|---|---|---|
| Adenosines | | |
| ATP | 1.28(5) | 0.065(1) |
| ADP | 0.85(2) | 0.058(1) |
| AMP | 0.397(5) | 0.053(1) |
| Guanosines | | |
| GTP | 33.1(1) | 0.099(1) |
| GDP | 9.84(5) | 0.164(3) |
| GMP | 2.84(1) | 0.118(2) |
| Cytosines | | |
| CTP | 0.103(7) | 0.006(1) |
| CDP | 0.149(9) | 0.008(1) |
| CMP | 0.139(6) | 0.008(1) |
| Uridines | | |
| UTP | 0.047(2) | 0.001(2) |
| UDP | 0.065(7) | 0.002(2) |
| UMP | 0.070(4) | 0.007(2) |

[a]Values in parentheses give the uncertainty for each value in units of least significant digits. Experimental conditions: Excitation at 346 nm, [Tb-DOTAm-Phen]3+: emission integrated from 450 nm-650 nm, Eu-DOTA-Phen: emission integrated from 550-750, time-delay 0.1 ms, [Tb-PhenDOTAM] or [Eu-DOTA-Phen] = 10 µM, water, [Tris] = 10 mM, pH 7.0, T = 20° C., errors represent standard deviation, n = 3.

Figure 25:
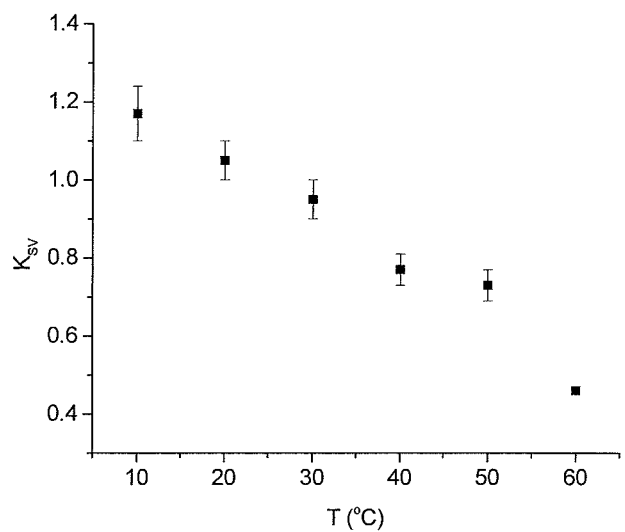
FIG. 25 is a graphical representation of Stern-Volmer constants of [Tb-DOTAm-Phen]$^{3+}$ with ATP as a function of temperature. Error bars represent standard deviation, n=3.

Notably, none of the twenty-four Stern-Volmer relationships measured curve upward as the concentration of nucleotide increases. Only one case, that of [Tb-DOTAm-Phen]$^{3+}$ with ATP, displays a slight negative curvature (decreasing $k_Q$) at high concentration of ATP (>2.0 mM). Such deviations are usually the result of the existence of multiple luminescing states, likely due to the formation of small aggregates (Boaz et al., *J. Am. Chem. Soc.*, 1950, 72, 3435-3443). The lack of any positive curvatures in the Stern-Volmer plots indicate that quenching is either purely static or purely dynamic in nature, but not both (Keizer, *J. Am. Chem. Soc.*, 1983, 105, 1494-1498). The two differing mechanisms can be distinguished by determining the effect of temperature on the Stern-Volmer constant. A purely static quenching is characterized by the formation of a non-emitting fluorophore.quencher complex which is entropically disfavored. The Stern-Volmer constant, $K_{SV}$, incorporates the association constant for this complex. Consequently as the temperature increases, the association constant of the fluorophore.quencher complex decreases and thus so does $K_{SV}$. On the other hand, in the case of dynamic or collisional quenching, the quencher must diffuse to the fluorophore during the lifetime of its excited state. In this case, as the temperature increases, the diffusion constant of the quencher also increases which in turn leads to increase in collisional quenching and $K_{SV}$. The Stern-Volmer constant of the positively charged molecular probe [Tb-DOTAm-Phen]$^{3+}$ with ATP decreases as the temperature increases (FIG. 25). (This data was acquired using only the linear part of the relationships.) The data thus clearly denotes a static mechanism of luminescence quenching and the formation of a fluorophore.quencher complex, in this case a phenanthridine.adenine interaction as depicted in FIG. 20a.

A strong indication that ATP or any other nucleotide is not directly coordinating the central lanthanide ion comes from the Stern-Volmer constants (Table 2). The affinities of [Tb-DOTAm-Phen]$^{3+}$ and Eu-DOTA-Phen for ATP, log $K_{SV}$=0.11 and −1.2, respectively, are six and seven orders of magnitude lower than that of the Eu aqua complex for the nucleotide as determined by Cleland (Morrison et al., *Biochemistry*, 1980, 19, 3127-3131). They are even substantially lower than that of biphosphate with the structurally similar complex Gd-DOTA (log $K_a$=2.2) (Dickins et al., *J. Am. Chem. Soc.*, 2002, 124, 12697-12705). The lower affinity constants suggest that the interactions at play are much weaker in nature than direct coordination of the nucleotides' phosphate.

Since it is apparent that the phosphate groups of the nucleotide do not coordinate to the lanthanide ion, the selectivity for ATP over ADP and AMP, as well as that for GTP over GDP and GMP, may result from weak electrostatic interactions between the negatively charged nucleotide and the positively charged [Tb-DOTAm-Phen]$^{3+}$. The higher the number of phosphates, the more negative the nucleotide, and the higher its affinity for the positive molecular probe. Previous reports have indicated that although weak, such interactions are nonetheless effective in water, particularly in the recognition of nucleotides and DNA. See, for example, Baudoin et al., *Chem.-Eur. J.*, 1999, 5, 2762-2771; Cudic et al., *J. Chem. Soc., Chem. Commun.*, 1995, 1073-1075; Dhaenens et al., *J. Chem. Soc., Perkin Trans.* 2, 1993, 1379-1381; Hosseini et al., *J. Am. Chem. Soc.*, 1990, 112, 3896-3904; and Zeglis et al., *J. Am. Chem. Soc.*, 2006, 128, 5654-5655.

Figure 42:
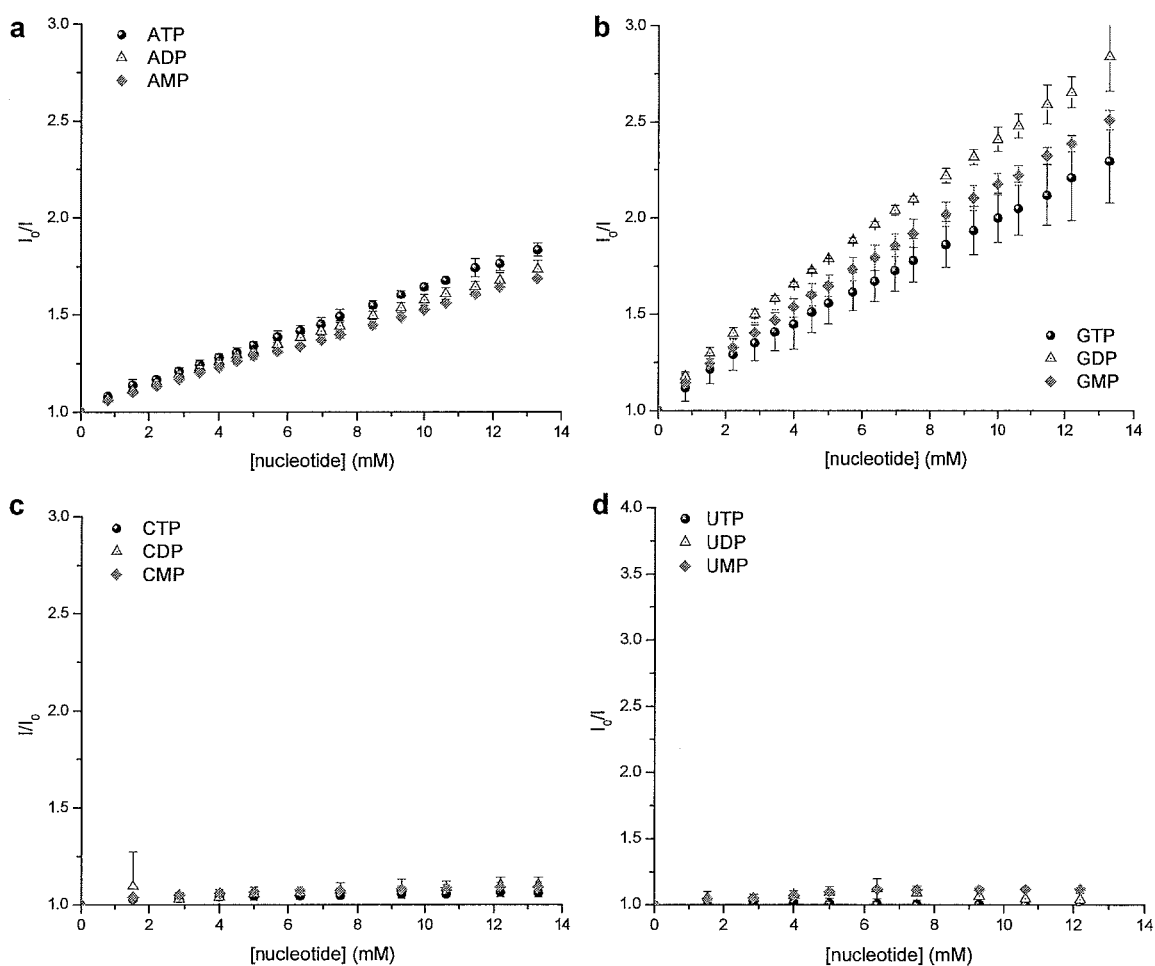
FIG. 42 illustrates Stern-Volmer plots of the time-delayed luminescence quenching of Eu-DOTA-Phen by a) adenosine, b) guanosine, c) cytosine and d) uridine nucleotides. Experimental conditions: excitation at 346 nm, time-delay 0.1 ms, emission slit width=5 nm, excitation slit width=5 nm, [Eu-DOTA-Phen]=10 μM, water, [Tris]=10 mM, pH 7.0, T=20° C.
Figure 43:
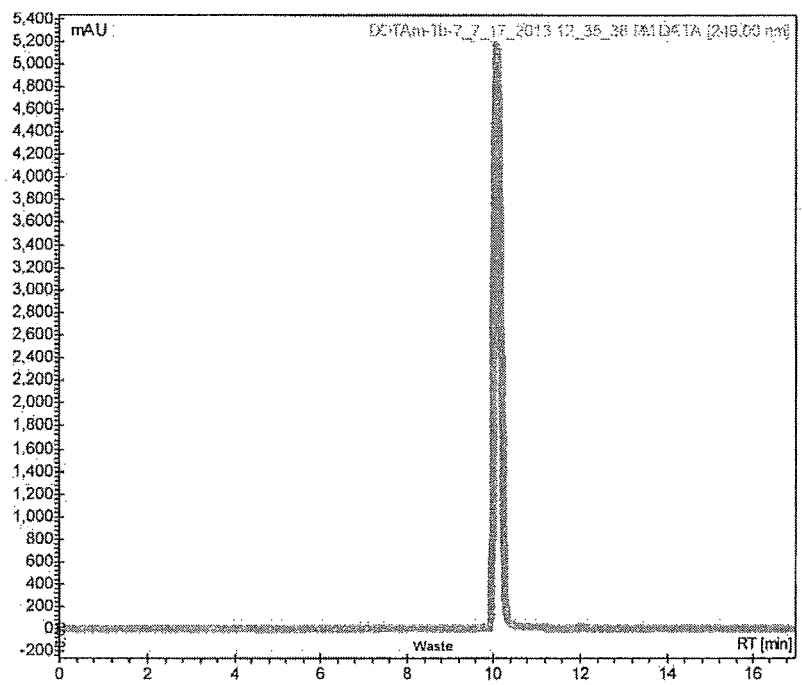
FIG. 43 illustrates and HPLC trace of Tb-DOTAm-Phen. Experimental conditions: Varian Microsorb 300-5 C18 250 mm×4.6 mm column, 1.0 mL/minute flow rate, solvent gradient: 100% 0.1% TFA (aq) to 40% 0.1% TFA (aq)/60% CH$_3$CN in 10 minutes, to 100% CH$_3$CN in 13 minutes.
Figure 44:
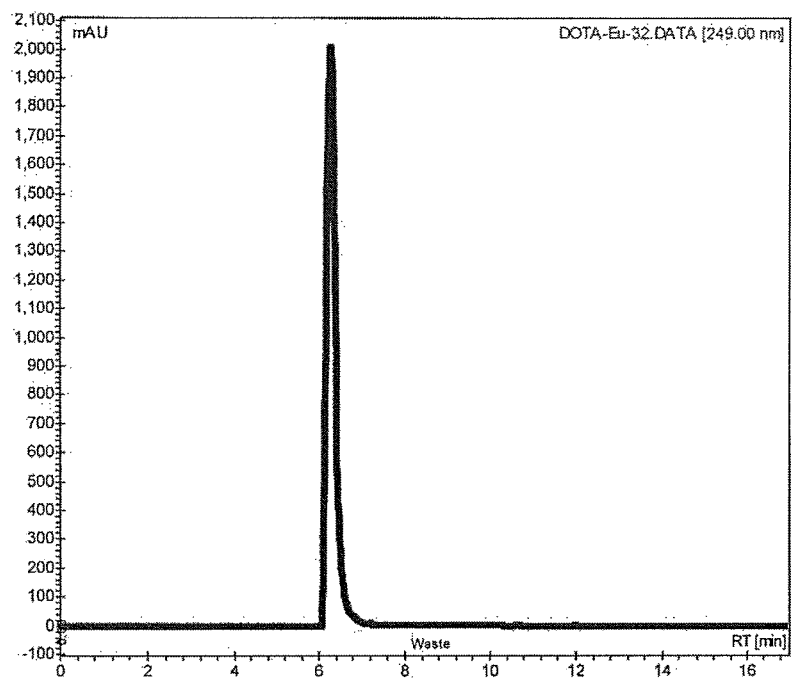
FIG. 44 illustrates an HPLC trace of Eu-DOTA-Phen. Experimental conditions: Varian Microsorb 300-5 C18 250 mm×4.6 mm column, 1.0 mL/minute flow rate, solvent gradient: 95% mQ water/5% CH$_3$CN to 40% mQ water/60% CH$_3$CN in 10 minutes, to 100% CH$_3$CN in 13 minutes.

The importance of weak electrostatic interactions in the recognition of ATP and GTP is directly apparent from the Stern-Volmer constants (Table 2). The +3 charged terbium-based molecular probe (1) consistently displays higher affinity for every nucleotide than the neutrally charged europium complex (12). Note that it is the charge of the complex and not the nature of the lanthanide which is at the root of this difference: the positively charged Eu(III) complex of the exact same DOTAm-Phen displays identical apparent binding constants as the Tb(III) complex of the same ligand, (1). In the case of GTP, the +3 charge of terbium probe (1) increases the apparent binding affinity by 300 fold over that of the neutral complex (12). Significantly, whereas the positively charged Tb(III) probe readily distinguishes between ATP, ADP and AMP (FIG. 17a) and between GTP, GDP and GMP (FIG. 26); the neutrally charged analog does not (see FIGS. 27 and 42a).

Figure 26:
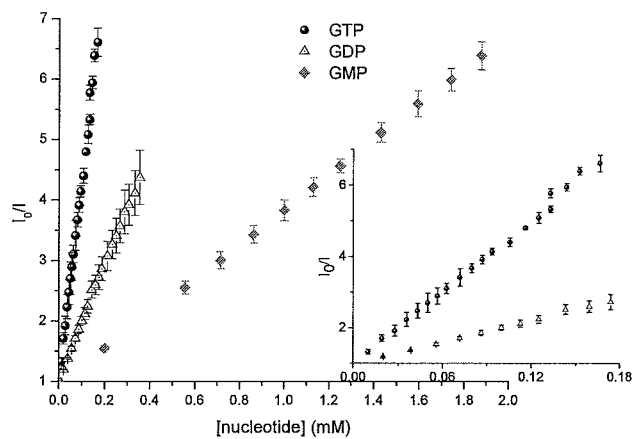
FIG. 26 illustrates a Stern-Volmer plot of the time-delayed luminescence of [Tb-DOTAm-Phen]$^{3+}$ (1) by the guanosine nucleotides GTP (filled circles), GDP (open triangles), and GMP (grey diamonds). Inset: zoom of data at low nucleotide concentration Experimental conditions: excitation at 346 nm, emission integrated from 450 to 650 nm, time-delay=0.1 ms, [Tb-DOTAm-Phen]$^{3+}$=10 μM, water, [Tris]=10 mM, pH 7.0, T=20° C., error bars represent standard deviation, n=3.
Figure 27:
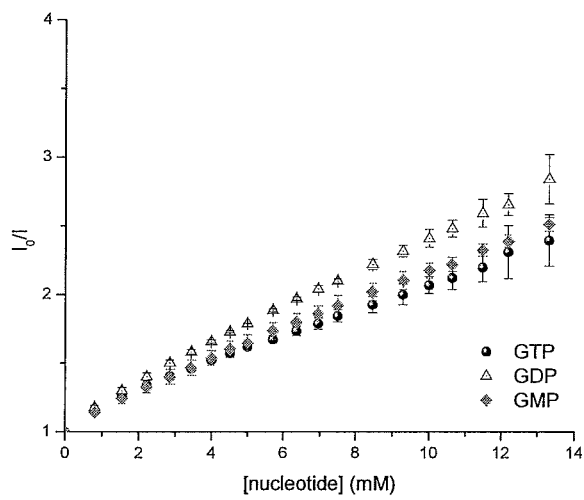
FIG. 27 illustrates a Stern-Volmer plot of the time-delayed luminescence of Eu-DOTA-Phen (12) by the guanosine nucleotides GTP (filled circles), GDP (open triangles), and GMP (grey diamonds). Experimental conditions: excitation at 346 nm, emission integrated from 550 to 750 nm, time-delay=0.1 ms, Eu-DOTA-Phen=10 μM, water, [Tris]=10 mM, pH 7.0, T=20° C., error bars represent standard deviation, n=3.

This observation strongly supports a model for the molecular recognition of nucleotides whereby the charge of the probe effectively distinguishes between tri-, di- and monophosphates (FIG. 26).

Figure 28:
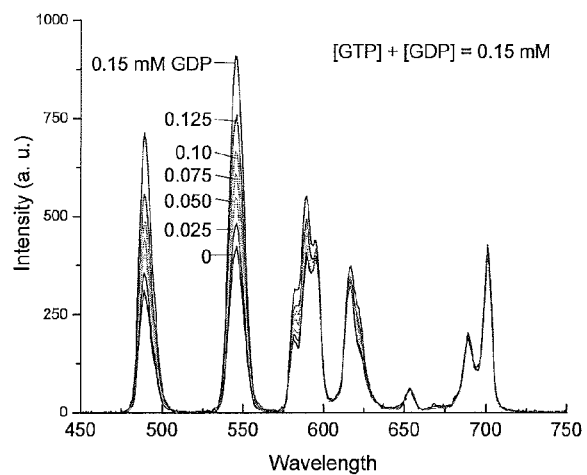
FIG. 28 illustrates a ratiometric determination of GTP to GDP conversion: time-delayed luminescence spectra of a solution [Tb-DOTAm-Phen]$^{3+}$ and Eu-DOTA-Phen in the presence of varying ratio of GTP:GDP. Experimental conditions: [Tb-DOTAm-Phen]$^{3+}$=10 μM, Eu-DOTA-Phen=10 μM, [GTP]+[GDP]=0.15 mM, [Tris]=10 mM, pH 7.0, T=20° C., excitation at 346 nm, time delay=0.1 ms. Concentration of GTP: 0-0.15 mM.

The two molecular probes, [Tb-DOTAm-Phen]$^{3+}$ and Eu-DOTA-Phen are both quenched in the presence of purine nucleotides, but they differ in that the positively charged terbium probe can distinguish between ATP and ADP or between GTP and GDP whereas the neutral europium complex cannot. These two probes further present other advantages which are characteristic of lanthanide-based molecular probes. First, both probes are excited at the same wavelength (346 nm). Therefore one can detect both probes mixed together in solution with a single emission spectrum. Moreover, lanthanides are characterized with very narrow (20 nm) emission bands; the main $^7F_5 \to {}^5D_4$ and $^7F_4 \to {}^5D_4$ emission peaks of the terbium (1) do not overlap with any emission peak of the europium (12). Furthermore, since f-f transitions, such as the one between the excited $^5D_4$ and $^5D_0$ states of terbium and europium, respectively, are Laporte-forbidden, they are known to occur only under conditions when the Eu—Tb distance is kept extremely short. See, for example, Rodrigues et al., *J. Phys. Chem. C*, 2012, 116, 19951-19957; Ramya et al., *Inorg. Chem.*, 2012, 51, 8818-8826; and Andolina et al., *Eur. J. Inorg. Chem.*, 2011, 2011, 154-164. In solution, the distances between two lanthanide complexes are realistically longer than what would lead to observable transfer, such that the green terbium probe does not sensitize the red europium one. As a result, unlike for organic dyes, when the two molecular probes are mixed in a solution, they both report on the presence of nucleotides independently of each other. Concomitant use of both probes advantageously allows for more precise ratiometric monitoring of enzymatic reactions. In order to monitor GTP to GDP conversion, for instance, the emission of the neutral Eu (12) at 689 and 701 nm indicates the total concentration of guanine nucleotide present in solution. The intensities of these peaks therefore remain constant during the reaction. The emissions of the positively charged Tb (1) at 490 and 545 nm then precisely indicate the ratio of GTP to GDP (FIG. 28) while the emissions at 699 nm indicate the total guanosine present.

One method to evaluate the suitability of a probe or of an assay for high-throughput screening or monitoring of enzyme kinetics is to calculate its Z-factor according to the following equation:

$$Z = 1 - \frac{3(\sigma_{max} + \sigma_{min})}{|\mu_{max} - \mu_{min}|}$$

where $\mu_{max}$ and $\mu_{min}$ are the mean maximum and minimum time-gated luminescence intensity (not $I_0/I$) and $\sigma_{max}$ and $\sigma_{min}$ are their respective standard deviations (Zhang et al., *J. Biomol. Screen.*, 1999, 4, 67-73).

For example, an assay for a GTPase starting with an initial GTP concentration of 0.150 mM, a value slightly lower than that typically find intracellularly (Traut, *Mol. Cell. Biochem.*, 1994, 140, 1-22) but more typical of HTS, and proceeding to 20% conversion of GTP to GDP would be characterized with a Z-factor of 0.686. Values between 0.5 and 1 are characteristic of excellent assays, suggesting that [Tb-DOTAm-Phen]$^{3+}$ could detect inhibitors of GTPases.

Figure 29:
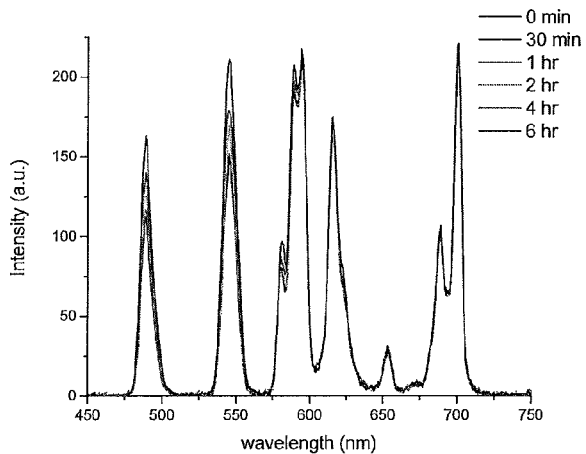
FIG. 29 illustrates an exemplary embodiment of continuous monitoring of ATP to ADP conversion during enzymatic phosphorylation of the peptide KRRWSAP-NH$_2$ by its kinase PKAc. Experimental conditions: [Tb-DOTAm-Phen]$^{3+}$=10 μM, Eu-DOTA-Phen=10 μM, [PKAc]=1 μM, [amide-blocked KRRWSAP-NH$_2$]=1.5 mM, [ATP]=1 mM, [Tris]=10 mM, [Brij-35]=0.05%, [MgCl$_2$]=50 mM, [EGTA]=5 mM, [DTT]=2 mM, pH 7.0, T=37° C., excitation at 346 nm, time delay=0.1 ms. Reaction time: 0-6 hours.
Figure 30:
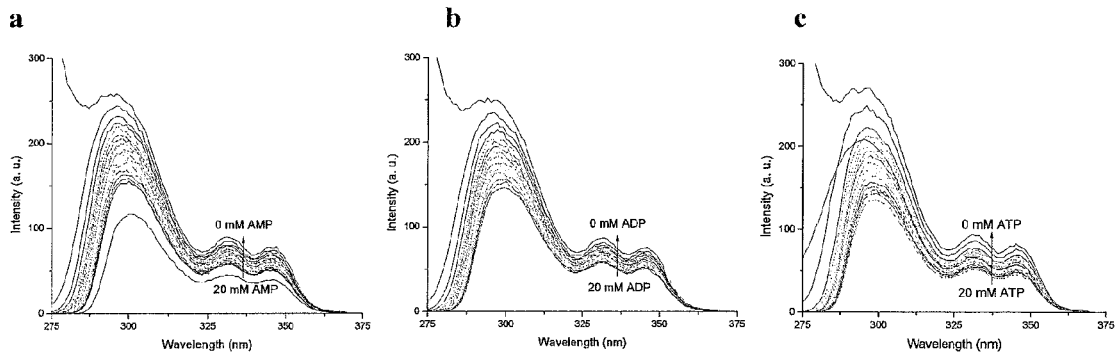
FIG. 30 illustrates time-delayed excitation spectra of a) Eu-DOTA-Phen.AMP, b) Eu-DOTA-Phen.ADP and c) Eu-DOTA-Phen.ATP titrations. Experimental conditions: emission at 545 nm, time-delay 0.1 ms, emission slit width=5 nm, excitation slit width=5 nm, [Eu-DOTA-Phen]=10 μM, water, [Tris]=10 mM, pH 7.0, T=20° C.
Figure 31:
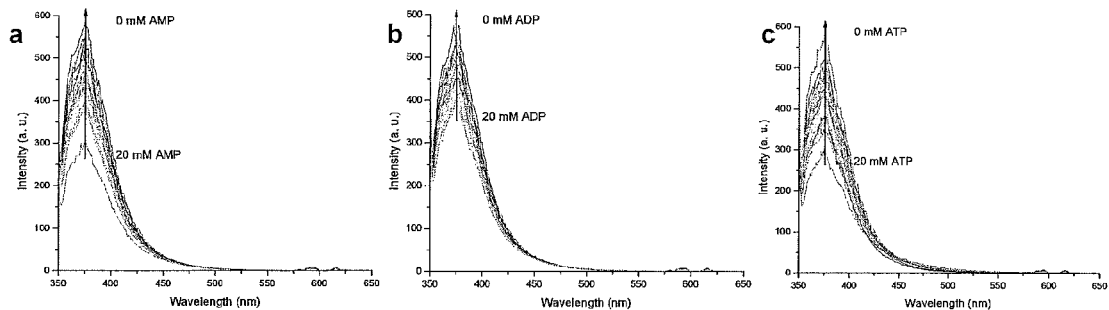
FIG. 31 illustrates fluorescence spectra of a) Eu-DOTA-Phen.AMP, b) Eu-DOTA-Phen.ADP and c) Eu-DOTA-Phen.ATP titrations. Experimental conditions: excitation at 346 nm, emission slit width=5 nm, excitation slit width=5 nm, [Eu-DOTA-Phen]=10 μM, water, [Tris]=10 mM, pH 7.0, T=20° C.
Figure 32:
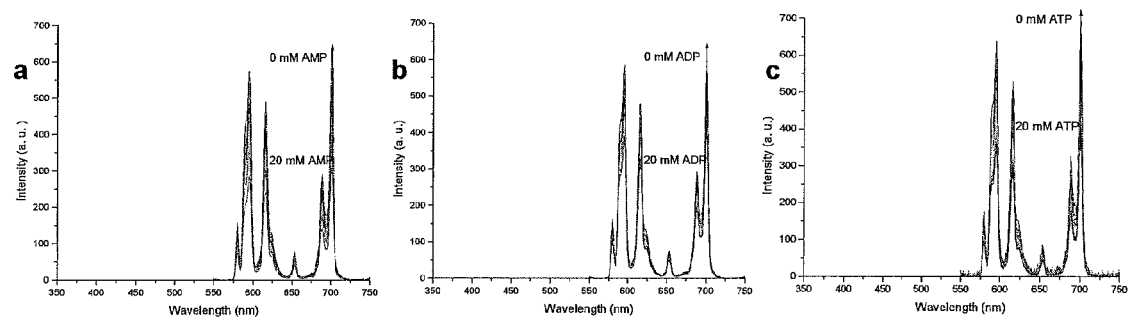
FIG. 32 illustrates time-delayed luminescence spectra of a) Eu-DOTA-Phen.AMP, b) Eu-DOTA-Phen.ADP and c) Eu-DOTA-Phen.ATP titrations. Experimental conditions: excitation at 346 nm, time-delay 0.1 ms, emission slit width=5 nm, excitation slit width=5 nm, [Eu-DOTA-Phen]=10 μM, water, [Tris]=10 mM, pH 7.0, T=20° C.
Figure 33:
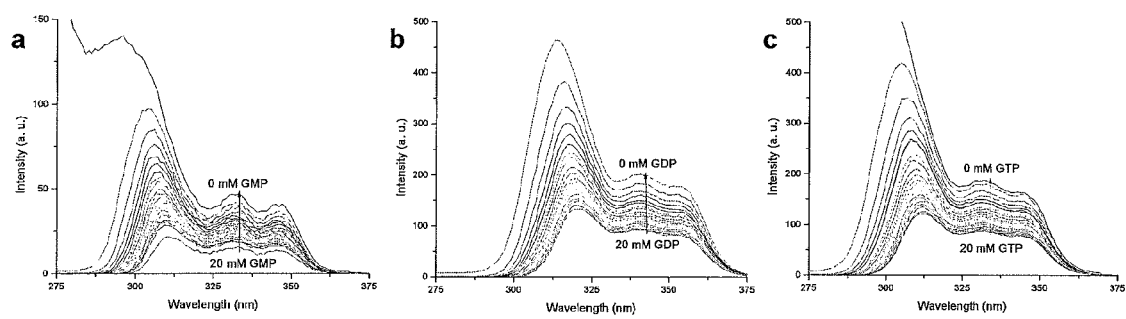
FIG. 33 illustrates time-delayed excitation spectra of a) Eu-DOTA-Phen.GMP, b) Eu-DOTA-Phen.GDP and c) Eu-DOTA-Phen.GTP titrations. Experimental conditions: emission at 545 nm, time-delay 0.1 ms, emission slit width=5 nm, excitation slit width=5 nm, [Eu-DOTA-Phen]=10 μM, water, [Tris]=10 mM, pH 7.0, T=20° C.
Figure 34:
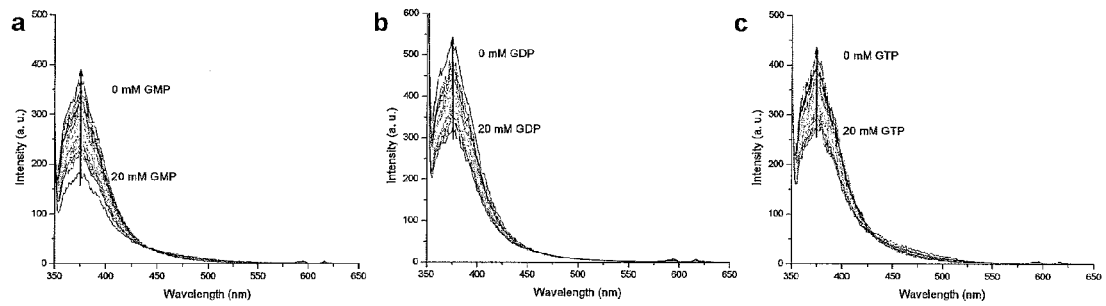
FIG. 34 illustrates fluorescence spectra of a) Eu-DOTA-Phen.GMP, b) Eu-DOTA-Phen.GDP and c) Eu-DOTA-Phen.GTP titrations. Experimental conditions: excitation at 346 nm, emission slit width=5 nm, excitation slit width=5 nm, [Eu-DOTA-Phen]=10 μM, water, [Tris]=10 mM, pH 7.0, T=20° C.
Figure 35:
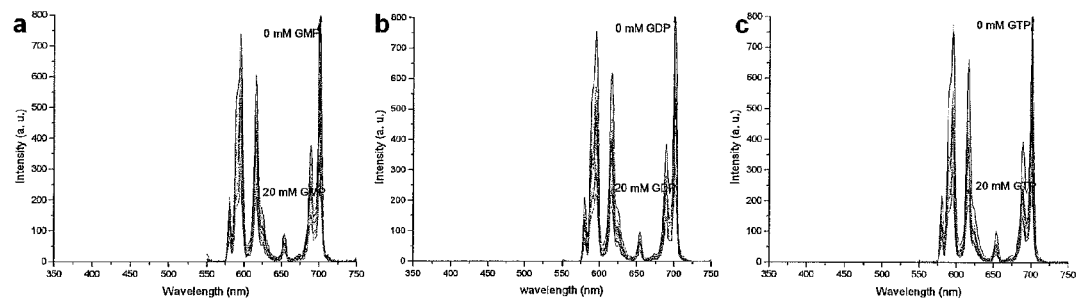
FIG. 35 illustrates time-delayed luminescence spectra of a) Eu-DOTA-Phen.GMP, b) Eu-DOTA-Phen.GDP and c) Eu-DOTA-Phen.GTP titrations. Experimental conditions: excitation at 346 nm, time-delay 0.1 ms, emission slit width=5 nm, excitation slit width=5 nm, [Eu-DOTA-Phen]=10 μM, water, [Tris]=10 mM, pH 7.0, T=20° C.
Figure 36:
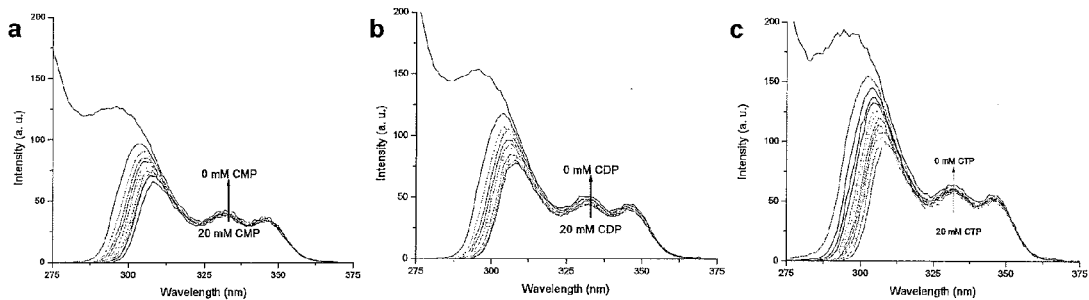
FIG. 36 illustrates time-delayed excitation spectra of a) Eu-DOTA-Phen.CMP, b) Eu-DOTA-Phen.CDP and c) Eu-DOTA-Phen.CTP titrations. Experimental conditions: emission at 545 nm, time-delay 0.1 ms, emission slit width=5 nm, excitation slit width=5 nm, [Eu-DOTA-Phen]=10 μM, water, [Tris]=10 mM, pH 7.0, T=20° C.
Figure 37:
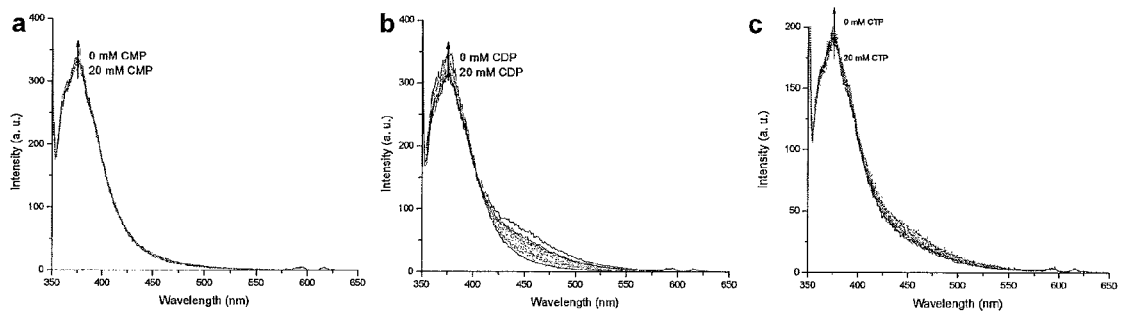
FIG. 37 illustrates fluorescence spectra of a) Eu-DOTA-Phen.CMP, b) Eu-DOTA-Phen.CDP and c) Eu-DOTA-Phen.CTP titrations. Experimental conditions: excitation at 346 nm, emission slit width=5 nm, excitation slit width=5 nm, [Eu-DOTA-Phen]=10 μM, water, [Tris]=10 mM, pH 7.0, T=20° C.
Figure 38:
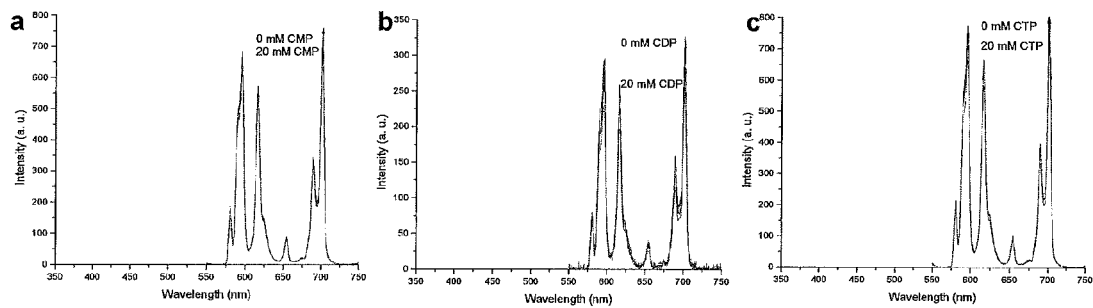
FIG. 38 illustrates time-delayed luminescence spectra of a) Eu-DOTA-Phen.CMP, b) Eu-DOTA-Phen.CDP and c) Eu-DOTA-Phen.CTP titrations. Experimental conditions: excitation at 346 nm, time-delay 0.1 ms, emission slit width=5 nm, excitation slit width=5 nm, [Eu-DOTA-Phen]=10 μM, water, [Tris]=10 mM, pH 7.0, T=20° C.
Figure 39:
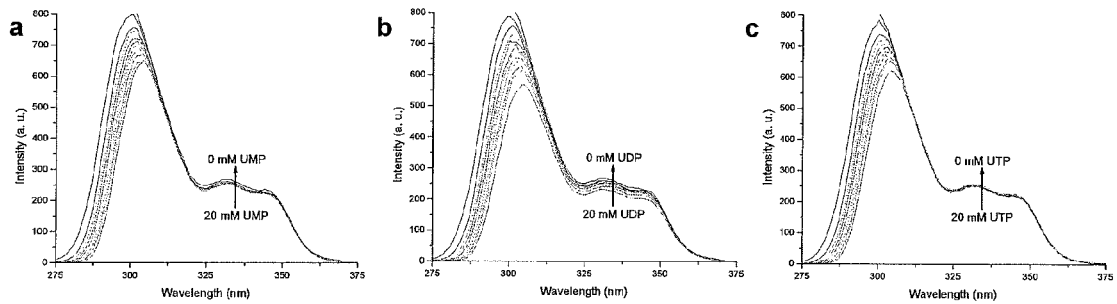
FIG. 39 illustrates time-delayed excitation spectra of a) Eu-DOTA-Phen.UMP, b) Eu-DOTA-Phen.UDP and c) Eu-DOTA-Phen.UTP titrations. Experimental conditions: emission at 545 nm, time-delay 0.1 ms, emission slit width=5 nm, excitation slit width=5 nm, [Eu-DOTA-Phen]=10 μM, water, [Tris]=10 mM, pH 7.0, T=20° C.
Figure 40:
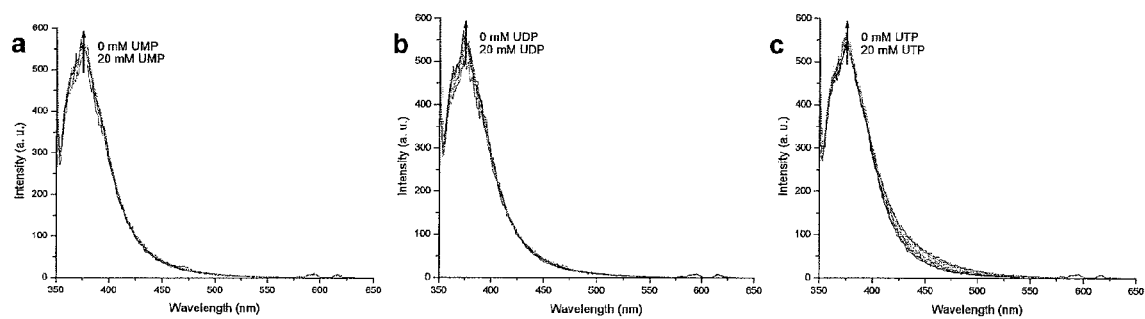
FIG. 40 illustrates fluorescence spectra of a) Eu-DOTA-Phen.UMP, b) Eu-DOTA-Phen.UDP and c) Eu-DOTA-Phen.UTP titrations. Experimental conditions: excitation at 346 nm, emission slit width=5 nm, excitation slit width=5 nm, [Eu-DOTA-Phen]=10 μM, water, [Tris]=10 mM, pH 7.0, T=20° C.
Figure 41:
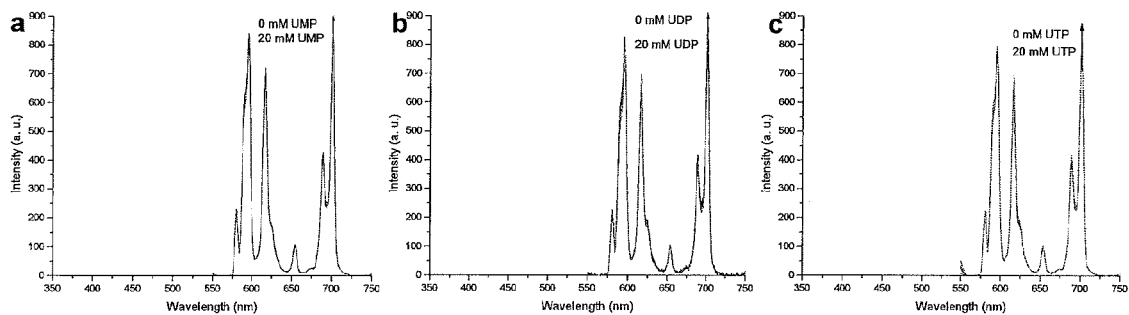
FIG. 41 time-delayed luminescence spectra of a) Eu-DOTA-Phen.UMP, b) Eu-DOTA-Phen.UDP and c) Eu-DOTA-Phen.UTP titrations. Experimental conditions: excitation at 346 nm, time-delay 0.1 ms, emission slit width=5 nm, excitation slit width=5 nm, [Eu-DOTA-Phen]=10 μM, water, [Tris]=10 mM, pH 7.0, T=20° C.

The ability of the two lanthanide probes to monitor enzymatic reactions involving ATP or GTP directly and continuously was evaluated with PKAc, the catalytic domain of protein kinase A. PKAc is a serine-threonine protein kinase that is actively studied as a biological target in cancer therapy (Naviglio et al., *Expert Opin. Ther. Targets*, 2009, 13, 83-92). PKAc assays are typically performed in a buffer that contains $MgCl_2$, EGTA, DTT and the detergent Brij-35; all of these components were found to be compatible with the use of probes as disclosed herein. Addition of either the kinase or its substrate, the amide-blocked peptide KRRWSAP-NH$_2$, in the absence of ATP does not affect the terbium nor the europium's luminescence, indicating that the probes are selective for the nucleotides and are not affected by the peptides. Phosphorylation of the substrate and conversion of ATP to ADP takes place only when all components are present in the buffer. As the reaction proceeds, the ADP:ATP ratio increases; as a result the terbium's luminescence at 490 nm and 545 nm increases whereas that of europium at 688 nm and 700 nm remains constant (FIG. 29). [Tb-DOTAm-Phen]$^{3+}$ and Eu-DOTA-Phen are thus able to directly monitor kinases' activities by time-gated luminescence spectroscopy. Beside time-gating, this assay possesses two advantages over existing technologies: it does not require a modified substrate, and it enables continuous monitoring of the reaction's kinetics. It should be noted, however, that these probes are not intended for use in cells as the presence of more than two purine nucleotides would make the results hard to interpret.

In summary, two molecular probes for the detection of ATP and GTP by time-gated luminescence are reported. The probes, [Tb-DOTAm-Phen]$^{3+}$ and Eu-DOTA-Phen, detect pyrimidines with complete selectivity over purines in a turn-off fashion. Since both the short-lived fluorescence of the antenna and the long-lived phosphorescence of the lanthanide are quenched, a ternary complex whereby the purine nucleobase is stacked on the phenanthridine antenna is proposed. This interpretation is in accordance with the temperature dependence of the Stern-Volmer constants which are characteristic of a static mechanism of quenching. Selectivity for purines over pyrimidines is likely the combination of both the lower affinity of the less extended pyrimidines, and of the lower energy level of the HOMO'S of cytosine and uracil which do not enable photoelectron transfer to the phenanthridine antenna. The two probes differ in only two ways: the nature of the lanthanide ion, which does not affect the selectivity or the affinity of the probe for its substrate, and the presence of amide arms that bestow the Rimier with positive charges. Although both complexes detect guanosines, and to a lesser extent adenosines, only the positively charged terbium one distinguishes between tri-, di- and monophosphates. The lack of selectivity of the neutrally charged Eu-DOTA-Phen for ATP and GTP over their lesser-charged analogs indicates that the response of the positively charged probe is likely the result of weak electrostatic interactions. Advantageously, the response of the Tb probe does not affect that of the Eu one. As such, they can be used concomitantly to accurately measure conversion of ATP to ADP or GTP to GDP ratiometrically, or under conditions where concentrations of the nucleotides may not be known initially. For instance, concomitant use of the two probes enables accurate and continuous monitoring of the phosphorylation of an unmodified peptide substrate by the kinase PKAc. The probes are thus useful for high-throughput screening and kinetic monitoring of the large number of enzymes utilizing nucleotides.

The present invention is illustrated by the following examples. It is to be understood that the particular examples, materials, amounts, and procedures are to be interpreted broadly in accordance with the scope and spirit of the invention as set forth herein.

EXAMPLES

General Considerations.

Unless otherwise noted, starting materials were obtained from commercial suppliers and used without further purification. Water was deionized and further purified by a Millipore cartridge system (resistivity $1.8 \times 10^7 \Omega$). All organic extracts were dried over anhydrous $MgSO_4$ and solvents were removed with a rotary evaporator. Flash chromatography was performed on Salicycle Silica Gel (230-400 mesh) or Brockmann activated aluminum oxide (neutral, 60 mesh). $^1H$ NMR spectra were recorded on a Varian 300 or Varian 500 at 300 MHz or 500 MHz, respectively, and $^{13}C$ NMR spectra on a Varian 300 at 75 MHz; the residual solvent peak was used as an internal reference. Data for $^1H$ NMR are recorded as follows: chemical shift ($\delta$, ppm), multiplicity (s, singlet; br s, broad singlet; d, doublet, t, triplet; q, quartet; m, multiplet), integration, coupling constant (Hz). Data for $^{13}C$ NMR are reported in terms of chemical shift ($\delta$, ppm). Mass spectra (LR=lo2w resolution; HR=high resolution; MS-ESI=electrospray mass spectrometry) were recorded on a Bruker BioTOF II. Purity of lanthanide complexes was evaluated by high performance liquid chromatography (HPLC) using a Varian Microsorb 300-5 C18 250 mm×4.6 mm at a flow rate was 1.0 mL/min (see supporting information for spectra and solvent gradients). UV-Vis data was obtained on a Cary Bio 100 UV-Vis Spectrophotometer. Data was collected over the range of 200-800 nm. Fluorescence data was acquired on a Varian Cary Eclipse Fluorescence Spectrophotometer using a quartz cell with a path length of 10 mm, excitation slit width of 5 nm and emission slit width of 5 nm at T=20° C. Solutions were not degased prior to measurement of their luminescence spectra and lifetimes.

Example 1

Experimental Procedures and Characterization Data for the Synthesis of the Complex Tb-PhenDOTAm (1)

2-Nitro-1,1'-biphenyl (2)

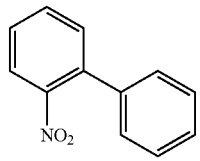 [SMILES: O=[N+]([O-])c1ccccc1-c1ccccc1]

Aqueous sodium carbonate (2 M, 100 mL), followed by tetrakis(triphenylphosphine) palladium (340. mg, 0.297 mmol), were added to a solution of 2-bromonitrobenzene (2.00 g, 9.90 mmol) and phenylboronic acid (1.27 g, 9.90 mmol) in dimethoxyethane (125 mL). The reaction mixture was heated to reflux for 3 hours. The reaction crude was then cooled to room temperature, diluted with water (100 mL) and the product extracted with $CH_2Cl_2$ (4×50 mL). The organic phase was dried over $MgSO_4$, and concentrated under reduced pressure to yield a yellow solid, which was further purified via flash chromatography over silica, eluting with a gradient of hexanes to 20% $CHCl_3$/80% hexanes. The nitro 2 was obtained as a yellow oil that was further dried under high vacuum for 24 h (1.79 g, 90.1%).

$^1H$ NMR (500 MHz, $CD_2Cl_2$) $\delta$ 7.33 (d, J=2.0 Hz, 1H), 7.35 (d, J=1.5 Hz, 1H), 7.42-7.48 (m, 4H), 7.52 (td, $J_1$=8.0 Hz, $J_2$=1.5 Hz, 1H), 7.65 (td, J=7.5, $J_2$=1.5, 1H), 7.86 (dd, $J_1$=8.0, $J_2$=1.0, 1H); $^{13}C$ NMR (75 MHz, $CD_2Cl_2$) $\delta$ 149.8, 138.1, 136.7, 133.0, 132.5, 129.2, 128.8, 128.7, 128.4, 124.6.

[1,1'-Biphenyl]-2-amine (3)

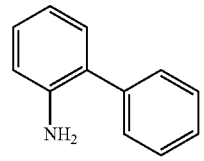 [SMILES: Nc1ccccc1-c1ccccc1]

Activated palladium on carbon (10% w/w, 0.25 g) was added to a solution of the nitro 2 (1.70 g, 8.53 mmol) in anhydrous methanol (100 mL). The reaction flask was purged thrice with $H_2$ (g), pressurized to 5 bar with $H_2$ (g), and mechanically shaken in a Parr hydrogenator for 12 hours. The reaction mixture was filtered and the filtrate was concentrated under reduced pressure to yield the amine 3 as a yellow oil (1.44 g, quant.) that was used immediately in the next step.

HRMS (ESI) calc for $[C_{12}H_{12}N]^+$ $([M+H]^+)$: m/z 170.0964. found: 170.0960.

N-([1,1'-biphenyl]-2-yl)acetamide (4)

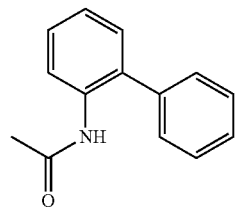 [SMILES: CC(=O)Nc1ccccc1-c1ccccc1]

Lithium hydroxide monohydrate (600 mg, 25.0 mmol) was added to a solution of the amine 3 (1.44 g, 8.53 mmol) dissolved in $CH_2Cl_2$ (125 mL) at 0° C. A solution of acetyl bromide (1.97 mL, 25.6 mmol) in $CH_2Cl_2$ (10 mL), was added dropwise over 5 minutes at 0° C. to the reaction mixture which was then allowed to warm to ambient temperature and stirred for 2 hours. The reaction crude was filtered, concentrated under reduced pressure, and purified by flash chromatography over silica, eluting with a gradient of 100% $CH_2Cl_2$ to 10% MeOH/90% $CH_2Cl_2$, yielding product 4 as white solid (1.11 g, 61.5%).

$^1H$ NMR (500 MHz, $CD_2Cl_2$) $\delta$ 1.93 (s, 3H), 7.26-7.34 (m, 5H), 7.39 (t, J=7.0 Hz, 3H), 7.46 (d, J=8.0 Hz, 1H); $^{13}C$ NMR (75 MHz, $CD_3OD$) $\delta$ 172.6, 140.7, 139.1, 135.5, 131.7, 130.2, 129.6, 129.1, 128.6, 128.3, 127.9, 119.7, 117.3, 23.0; HRMS (ESI) calc for $[C_{14}H_{14}NO]^+$ $([M+H]^+)$: m/z 212.1070. found: 212.1072.

6-Methylphenanthridine (5)

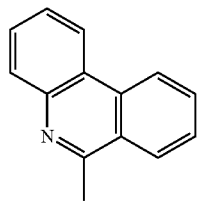

A mixture of the acetamide 4 (717 mg, 3.39 mmol) and finely grinded polyphosphoric acid (10 mL, 115% $H_3PO_4$ equiv.) was stirred at 150° C. for 2.5 hours. The reaction mixture was then cooled to 0° C. and slowly basified to pH 14 with saturated NaOH (aq). The mixture was extracted with $CH_2Cl_2$ (4×30 mL), and the organic phase dried with $MgSO_4$. Evaporation of the solvent under reduced pressure, followed by flash chromatography over silica, eluting with a gradient of 100% $CH_2Cl_2$ to 10% MeOH/90% $CH_2Cl_2$, yielded the phenanthridine 5 as a crystalline white solid (567 mg, 86.6%).

$^1$H NMR (500 MHz, $CDCl_3$) δ 3.06 (s, 3H), 7.63 (td, $J_1$=7.5 Hz, $J_2$=1.5 Hz, 1H), 7.71 (ddddd, $J_1$=11.0 Hz, $J_2$=10.0 Hz, $J_3$=4.0 Hz, $J_4$=1.5 Hz, $J_5$=1.0 Hz, 2H), 7.85 (ddd, $J_1$=8.5 Hz, $J_2$=7.0 Hz, $J_3$=1.5 Hz, 1H), 8.11 (dd, $J_1$=8.0 Hz, $J_2$=1.0 Hz, 1H), 8.23 (dq, $J_1$=8.5 Hz, $J_2$=0.5 Hz, 1H), 8.55 (dd, $J_1$=8.0 Hz, $J_2$=1.5 Hz, 1H), 8.64 (dt, $J_1$=8.0, $J_2$=0.5, 1H); $^{13}$C NMR (75 MHz, $CDCl_3$) δ 159.2, 135.8, 132.9, 130.8, 129.9, 129.7, 129.0, 127.7, 126.9, 126.7, 126.2, 122.7, 122.3, 23.8;

HRMS (ESI) calc for $[C_{15}H_{11}N]^+$ ($[M+H]^+$): m/z 194.0964. found: 194.0972.

6-(Bromomethyl)phenanthridine (6)

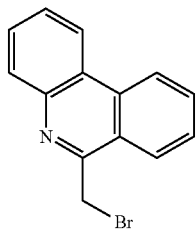 [SMILES: BrCc1nc2ccccc2c2ccccc12]

N-bromosuccinimide (557 mg, 3.13 mmol) was added to a solution of the phenanthridine 5 (403 mg, 2.09 mmol) in benzene (20 mL) and the reaction mixture was stirred while lit with a tungsten lamp (150 W) for 45 minutes. The reaction crude, including precipitated succinimide, was deposited onto silica and purified by flash chromatography eluting with $CH_2Cl_2$. Evaporation of the solvent under reduced pressure yielded the bromo 6 as a white solid (495 mg, 87.1%).

$^1$H NMR (500 MHz, $CDCl_3$) δ 5.11 (s, 2H), 7.70 (td, $J_1$=7.0 Hz, $J_2$=1.0 Hz, 1H), 7.76 (qd, $J_1$=8.0 Hz, $J_2$=1.0 Hz, 2H), 7.89 (t, J=8.0 Hz, 1H), 8.17 (d, J=7.5 Hz, 1H), 8.37 (d, J=8.0 Hz, 1H), 8.58 (d, J=8.0 Hz, 1H), 8.68 (d, J=8.5 Hz, 1H); $^{13}$C NMR (75 MHz, $CDCl_3$) δ 156.2, 142.5, 133.9, 131.7, 129.6, 129.4, 128.2, 127.9, 126.8, 124.7, 124.0, 122.9, 122.3, 31.2; HRMS (ESI): calc for $[C_{15}H_{10}BrN]^+$ ($[M+H]^+$): m/z 272.0069. found: 272.0081.

6-(Azidomethyl)phenanthridine (7)

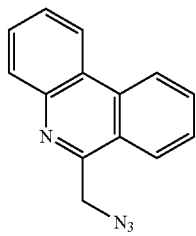 [SMILES: [N-]=[N+]=NCc1nc2ccccc2c2ccccc12]

Sodium azide (715 mg, 11.0 mmol) was added to a solution of the bromide 6 (301 mg, 1.10 mmol) in dry acetone (30 mL). The reaction mixture was stirred at ambient temperature for 1 hour, then heated to reflux for 2 hours. The reaction mixture was then allowed to cool to room temperature, the excess sodium azide was filtered off, and the solvent was removed under reduced pressure to yield the crude azide 7 as a light yellow crystalline solid, which was used immediately in the next step without further purification.

$^1$H NMR (500 MHz, $CD_3OD$) δ 5.05 (s, 2H), 7.75 (td, $J_1$=7.0 Hz, $J_2$=1.5 Hz, 1H), 7.80 (qd, $J_1$=8.0 Hz, $J_2$=1.0 Hz, 2H), 7.97 (td, $J_1$=7.0 Hz, $J_2$=1.0 Hz, 1H), 8.15 (dd, $J_1$=8.0 Hz, $J_2$=1.0 Hz, 1H), 8.33 (d, J=8.0 Hz, 1H), 8.73 (d, J=8.5 Hz, 1H), 8.83 (d, J=8.5 Hz, 1H). $^{13}$C NMR (75 MHz, $CD_3OD$) δ 56.3, 125.0, 125.2, 126.9, 127.1, 128.7, 130.3, 130.5, 131.6, 131.8, 134.1, 136.0, 145.5, 158.34.

Phenanthridin-6-ylmethanamine (8)

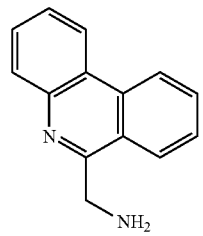 [SMILES: NCc1nc2ccccc2c2ccccc12]

Activated palladium on carbon (10% w/w, 26 mg) was added to a solution of the azide 7 (258 mg, 1.10 mmol) in MeOH (40 mL). The reaction flask was purged thrice with $H_2$ (g), pressurized to 4 bar with $H_2$ (g), and mechanically shaken in a Parr hydrogenator for 3.5 hours. The reaction mixture was filtered. The filtrate was concentrated under reduced pressure to yield amine 8 as a yellow oil that was used immediately in the next step without further purification.

2-Chloro-N-(phenanthridin-6-ylmethyl)acetamide (9)

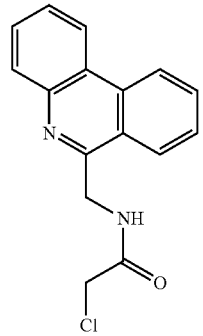 [SMILES: O=C(CCl)NCc1nc2ccccc2c2ccccc12]

Triethylamine (460 μL, 3.30 mmol), followed by a solution of chloroacetyl chloride (175 μL, 2.20 mmol) in $CH_2Cl_2$ (5 mL) were added dropwise over 5 minutes to a solution of the amine 8 (229 mg, 1.10 mmol) dissolved in $CH_2Cl_2$ (15 mL) at 0° C. The reaction mixture was then allowed to warm to ambient temperature and stirred for 2 hours. The solvent was removed under reduced pressure and the reaction crude purified via flash chromatography over silica eluting with a gradient of $CH_2Cl_2$ to 1% MeOH/99% $CH_2Cl_2$. Evaporation of the solvents under reduced pressure yielded the chloro 9 as an off-white solid (177 mg, 56.5% over three steps).

$^1$H NMR (500 MHz, $CD_3OD$) δ 4.20 (s, 2H), 4.89 (s, 2H), 7.76 (td, $J_1$=8.5 Hz, $J_2$=1.5 Hz, 1H), 7.81, (td, $J_1$=7.0 Hz, $J_2$=1.5 Hz, 1H), 7.85 (td, $J_1$=7.5 Hz, $J_2$=1.0 Hz, 1H), 7.93 (ddd, J=6.5 Hz, $J_2$=3.0 Hz, $J_3$=2.0 Hz, 1H), 8.23 (d, J=7.5 Hz, 1H), 8.75 (d, J=8.5 Hz, 1H), 8.77 (d, J=8.5 Hz, 1H), 8.86 (d, J=8.5 Hz, 1H); $^{13}$C NMR (75 MHz, $CDCl_3$), δ 42.7, 43.2, 122.5, 123.0, 124.2, 124.3, 124.8, 127.6, 128.2, 129.3, 129.9, 131.5, 133.2, 153.7, 156.6, 166.5; MS (ESI) calc for $[C_{16}H_{14}ClN_2O]^+$ ($[M+H]^+$): m/z 285.08. found: 285.09.

N-(phenanthridin-6-ylmethyl)-2(1,4,7,10-tetraazacyclododecan-1-yl)acetamide (10)

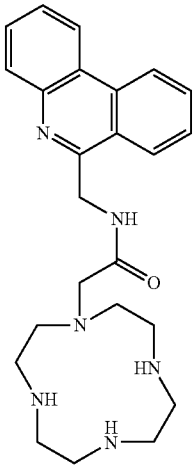 [SMILES: O=C(CN1CCNCCNCCNCC1)NCc1nc2ccccc2c2ccccc12]

A solution of the chloro 9 (20.0 mg, 70.2 μmol) in anhydrous $CHCl_3$ (5 mL) was added to a solution of cyclen (48.4 mg, 0.281 mmol) and triethylamine (11.7 μL, 84.2 μmol) in anhydrous $CHCl_3$ (15 mL) under $N_2$ (g). The reaction mixture was heated to reflux under $N_2$ (g) for 23 hours. The reaction mixture was then allowed to cool to room temperature and washed with NaOH (aq) (1.0 M, 3×5 mL) and $H_2O$ (3×5 mL). The organic phase was dried over $MgSO_4$, and concentrated under reduced pressure yielding product 10 as a colorless oil (13.9 mg, 47.1%). This procedure follows closely that developed by Gunnlaugsson and coworkers. (Massue et al. *Tetrahedron Lett.*, 2007, 48, 8052-8055).

$^1$H NMR (500 MHz, $CDCl_3$) δ 2.51-2.57 (br m, 4H), 2.61-2.67 (br m, 4H), 2.72 (s, 2H), 2.73-2.80, (br m, 8H), 3.38 (s, 2H), 5.21 (d, J=5 Hz, 2H) 7.66 (td, $J_1$=7.0 Hz, $J_2$=1.0 Hz, 1H), 7.73 (td, $J_1$=7.5 Hz, $J_2$=1.5 Hz, 2H), 7.87 (t, J=8.0 Hz, 1H), 8.14 (d, J=8.0 Hz, 1H), 8.26 (d, J=8.5 Hz, 1H), 8.56 (d, J=8.0 Hz, 1H), 8.64 (d, J=8.0 Hz, 1H); $^{13}$C NMR (75 MHz, $CDCl_3$), δ 42.5, 45.7, 45.9, 46.0, 47.1, 52.9, 59.8, 121.9, 122.2, 123.8, 124.1, 125.1, 126.8, 127.6, 128.4, 129.2, 130.7, 132.5, 142.8, 155.8, 171.4.

DOTAm-Phen-2,2',2''-(10-(2-oxo-2-(phenanthridin-6-ylmethylamino)ethyl)-1,4,7,10-tetraazacyclododecane-1,4,7-triyl)tris(N-methylacetamide) (11)

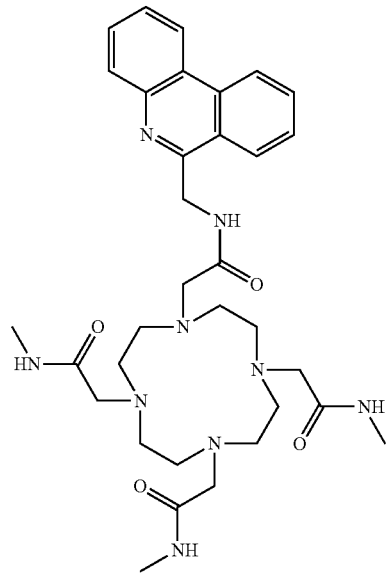

$Cs_2CO_3$ (77.6 mg, 238 pimp followed by 2-chloro-N-methylacetamide (16.9 mg, 157 μmol) were added to a solution of the cyclen derivative 10 (20.0 mg, 47.6 μmol) in anhydrous acetonitrile (5 mL). The reaction flask was purged thrice with $N_2$ (g) and the reaction mixture was heated to reflux for 34 h under $N_2$. (g). The reaction mixture was then filtered. The filtrate was concentrated under reduced pressure, and the product was purified by chromatography over alumina, eluting with 1% MeOH/99% $CH_2Cl_2$ to yield a colorless oil. The oil was then dissolved in $H_2O$ (5 mL) and lyophilized to yield product 11 as a white powder (6.37 mg, 21.1%).

$^1$H NMR (500 MHz, $D_2O$) δ 2.58-3.05 (m, 31H), 3.29 (t, J=7.5 Hz, 2H), 4.07 (s, 2H), 4.61 (s, 2H), 7.82 (t, J=7.5 Hz, 3H), 8.02, (t, J=7.0, 1H), 8.34 (d, J=7.5 Hz, 1H), 8.43 (d, J=6.5 Hz, 1H), 8.68 (d, J=7.5 Hz, 1H), 8.79 (d, J=6.5 Hz, 1H);

HRMS (ESI) calc for $[C_{33}H_{47}N_9O_4Na]^+$ ($[M+Na]^+$): m/z 656.3643. found: 656.3641.

Tb-PhenDOTAm (1)

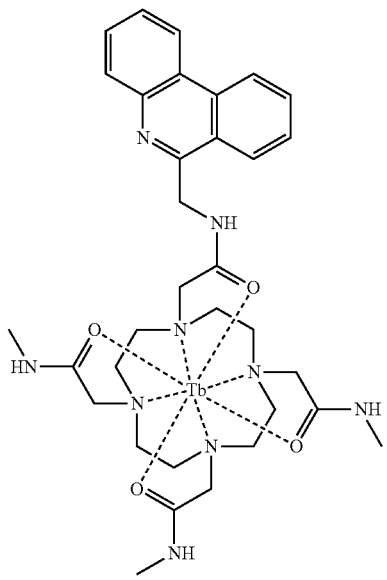

Figure 4:
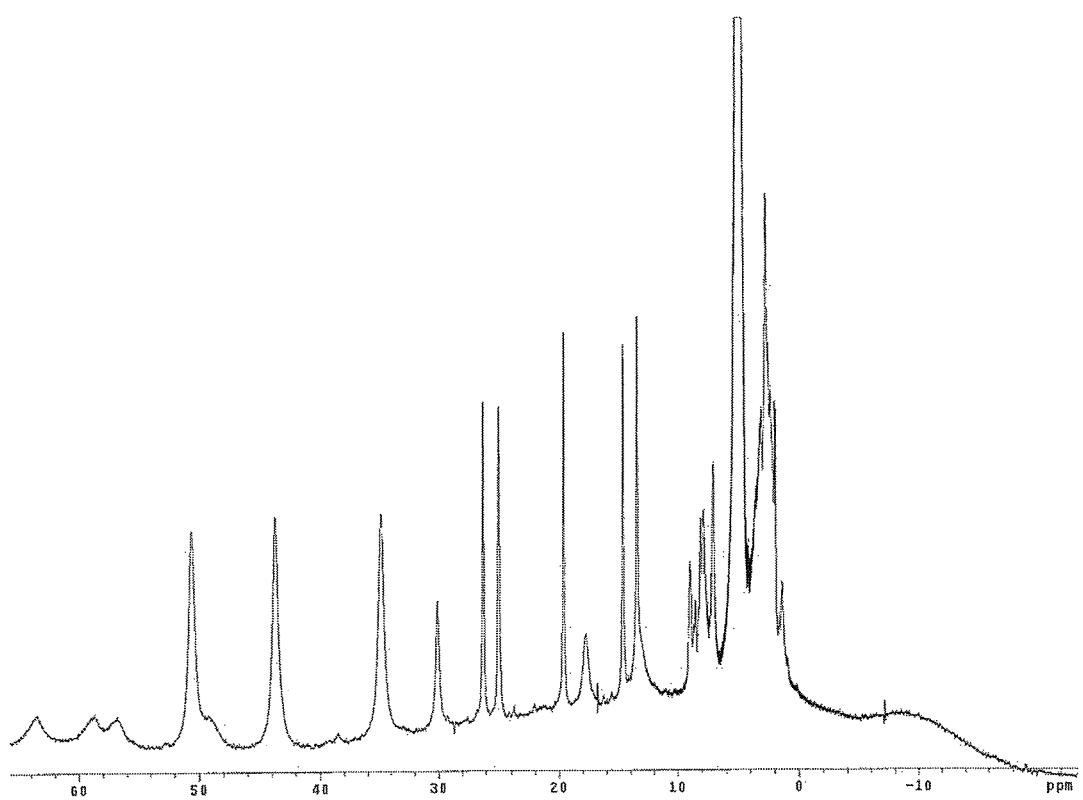
FIG. 4 shows the $^1H$ NMR spectra of the complex Tb-PhenDOTAm (1, $D_2O$, 500 MHz).
Figure 5:
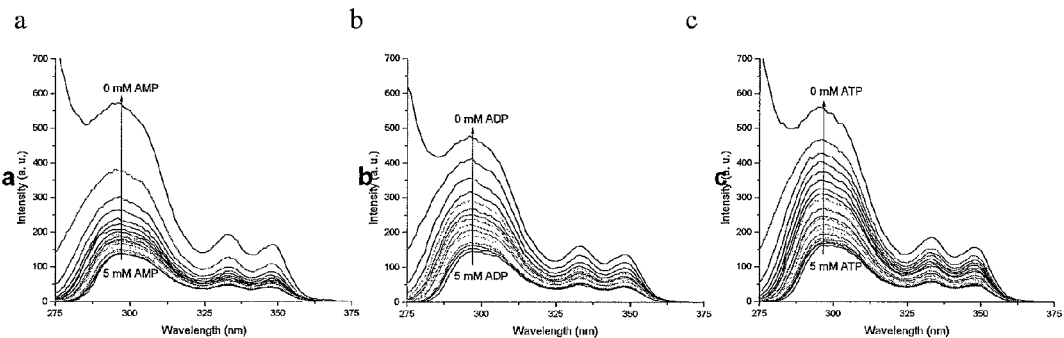
FIG. 5 illustrates time-delayed excitation spectra of a) Tb-PhenDOTAm.AMP, b) Tb-PhenDOTAm.ADP and c) Tb-PhenDOTAm.ATP titrations. Experimental conditions: emission at 545 nm, time-delay 0.1 ms, emission slit width=5 nm, excitation slit width=5 nm, [Tb-PhenDOTAm]=10 μM, water, [Tris]=10 mM, pH 7.0, T=20° C.

TbCl$_3$ (0.318 mg, 1.20 µmol) was added to a solution of the ligand DOTAm-Phen (11, 0.760 mg, 1.20 µmol) in H$_2$O (5 mL). The pH of the solution was adjusted to pH 8 with LiOH, and the reaction mixture was heated to 70° C. for 17 hours, yielding the complex 1. See FIG. 4 for $^1$H NMR.

HRMS (ESI) calc for $[C_{33}H_{47}N_9O_4Tb]^{2+}$ ($[M-H]^{2+}$): m/z 395.6463. found: 395.6465.

Example 2

Experimental Procedures and Characterization Data for the Synthesis of the Complex Eu-DOTA-Phen (12)

Tri-tert-butyl 2,2',2''-(10-(2-oxo-2-((phenanthridin-6-ylmethyl)amino)ethyl)-1,4,7,10-tetraazacyclododecane-1,4,7-triyl)triacetate (13)

Tri-tert-butyl 2,2',2''-(1,4,7,10-tetraazacyclododecane-1,4,7-triyl)triacetate (33.5 mg, 65.1 mop was dissolved in dry CH$_3$CN (10 mL) and magnetically stirred under N$_{2(g)}$. Anhydrous K$_2$CO$_3$ (30.0 mg, 0.217 mmol) was added, followed by 2-chloro-N-(phenanthridin-6-ylmethyl)acetamide (Weitz et al., *J. Am. Chem. Soc.*, 2012, 134, 16099-16102) (15.4 mg, 54.2 mmol) dissolved in 15 mL CH$_3$CN/DMF (2:1), and the reaction mixture was heated to reflux for 27 hours under N$_{2(g)}$. The reaction mixture was then filtered and concentrated under reduced pressure to yield a colorless glass that was used without further purification in the next step. $^1$H NMR (500 MHz, CDCl$_3$) δ 1.45 (s, 27H), 2.70-3.21 (m, 16H), 3.37-3.42 (m, 6H), 5.41 (d, J=15 Hz, 2H), 7.66-7.87 (m, 3H), 8.02 (d, J=7.0 Hz, 1H), 8.22 8.28 (d, J=6.5 Hz, 1H), 8.55 (d, J=8.0 Hz, 1H), 8.63 (d, J=7.5 Hz, 1H), 8.77 (d, J=7.0 Hz, 1H). HRMS (ESI): calc for $[C_{42}H_{62}N_6O_7]^+$ ($[M+H]^+$): m/z 763.4753. found: 763.4739.

2,2',2''-(10-(2-oxo-2-((phenanthridin-6-ylmethyl)amino)ethyl)-1,4,7,10-tetraazacyclododecane-1,4,7-triyl)triacetic acid (DOTA-Phen, 14)

The $^t$Bu ester 13 (92.3 mg, 121 µmol) was dissolved in CH$_2$Cl$_2$ (10 mL) and magnetically stirred under N$_{2(g)}$ in an ice bath. Trifluoroacetic acid (4 mL) was then added dropwise over 2 min, after which the reaction mixture was allowed to warm to ambient temperature and stirred for 65 hours. The reaction mixture was then concentrated under reduced pressure and excess TFA was driven off with subsequent portions of cold MeOH (3×3 mL) followed by concentration under reduced pressure. The resultant colorless glass was taken up in mQ H$_2$O (2 mL), diluted with CH$_3$CN (2 mL) and purified via HPLC, eluting with a gradient of 0-100% CH$_3$CN in mQ H$_2$O over 40 min (T$_r$=23.5-24.5 min, column: Agilent Microsorb C18 250×10 mm) and lyophilized to yield 14 as a hygroscopic white powder. $^1$H NMR (500 MHz, D$_2$O) δ 2.66-3.55 (m, 12H), 3.69-3.84 (m, 6H), 5.55 (s, 2H), 7.90-8.00 (m, 3H), 8.12 (d, J=7.0 Hz, 1H), 8.22 (t, J=8.0 Hz, 1H), 8.52 (d, J=8 Hz, 1H), 8.72 (d, J=7.5 Hz, 1H), 8.78 (d, J=7.0 Hz, 1H). $^{13}$C NMR (125 MHz, CD$_3$OD), δ 42.5, 54.5, 54.7, 54.8, 55.1, 56.7, 62.4, 68.2, 83.3, 95.0, 115.9, 116.3, 118.5, 126.2, 130.8, 132.4, 134.5, 135.5, 140.2, 148.8, 149.1, 154.8, 155.8, 161.6, 175.6, 175.9. HRMS (ESI) calc for $[C_{30}H_{39}N_6O_7]^+$ ($[M+H]^+$): m/z 595.2875. found: 595.2862.

Eu-DOTA-Phen (12)

The ligand 14 (9.87 mL of a 0.614 mM stock solution standardized by UV-Vis, 6.06 µmol) was dissolved in mQ H$_2$O (2 mL) and magnetically stirred. Aqueous EuCl$_3$ (18.2 µL of a 98.7 mM stock solution, 6.06 µmol) was then added, and the pH adjusted to 8 with LiOH$_{(s)}$. The reaction mixture was then heated to reflux for 19 hours and lyophilized to yield 12 as a colorless powder (4.89 mg, 6.06 µmol, quant. yield). HRMS (ESI): calcd. for $[C_{30}H_{36}EuN_6O_7]^+$ ($[M+H]^+$): m/z 745.1852. found: 745.1842. The observed isotopic pattern matched the calculated one.

The complete disclosure of all patents, patent applications, and publications, and electronically available material (e.g., GenBank amino acid and nucleotide sequence submissions; and protein data bank (pdb) submissions) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A luminescent probe comprising a structure of the formula:

Formula I

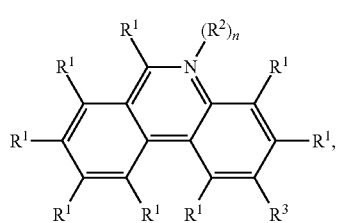

wherein:
each $R^1$ represents hydrogen, a C1-C10 hydrocarbon moiety, a halogen, or Z;

$R^2$ represents hydrogen or a C1-C10 hydrocarbon moiety group;

$R^3$ represents hydrogen, a C1-C10 hydrocarbon moiety, or a halogen;

wherein for molecules in which one or more of $R^1$, $R^2$, and/or $R^3$ represents a C1-C10 hydrocarbon moiety, two or more of $R^1$, $R^2$, and $R^3$ may optionally be joined with one another to form one or more fused rings;

n=0 or 1; and

Z represents a chelated luminescent Lanthanide (Ln) complex attached to the phenanthridine with a $-C(R^5)_2NHC(O)CH_2$-Lanthanide (Ln) complex linkage, wherein each $R^5$ independently represents hydrogen with the proviso that one $R^1$=Z.

2. The luminescent probe of claim 1 wherein the chelated Lanthanide complex comprises a polyamino carboxamide chelated Lanthanide, wherein the polyamino carboxamide chelator is selected from the group consisting of a 1,4,7,10-tetraazacyclododecane-1,4,7,10-tetraacetamide (DOTAm) chelator and a diethylene triamine pentaacetamide (DTPAm) chelator.

3. The luminescent probe of claim 2 wherein Z represents a group of the Formula Z1:

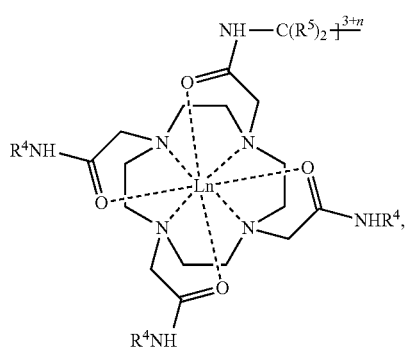

wherein each $R^4$ and $R^5$ independently represent H.

4. The luminescent probe of claim 3 wherein each $R^4$ represents a methyl group, and each $R^5$ represents hydrogen.

5. The luminescent probe of claim 2 wherein Z represents a group of the Formula Z2:

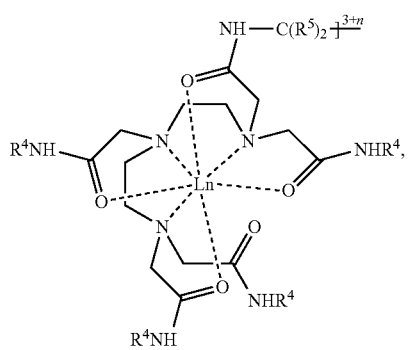

wherein each $R^4$ and $R^5$ independently represent H.

6. The luminescent probe of claim 5 wherein each $R^4$ represents a methyl group, and each $R^5$ represents hydrogen.

7. The luminescent probe of claim 1 wherein the Lanthanide is selected from the group consisting of La, Ce, Pr, Nd, Pm, Sm, Eu, Tb, Dy, Ho, Er, Tm Yb, Lu, or combinations thereof.

8. The luminescent probe of claim 1 wherein:

each $R^1$ represents hydrogen or Z;

$R^3$ represents hydrogen;

n=0; and

Z represents a chelated luminescent Terbium (Tb) complex, with the proviso that one $R^1$=Z.

9. The luminescent probe of claim 1 comprising a structure of the formula:

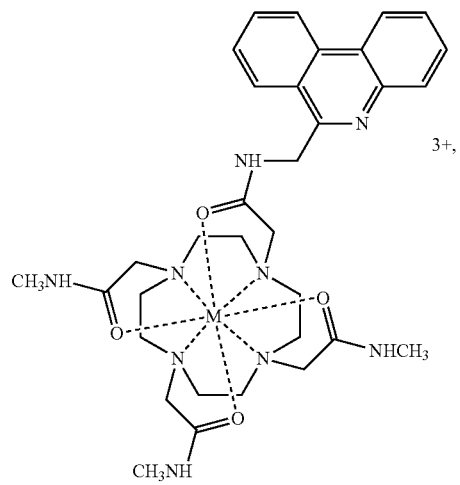

Formula II wherein M represents Tb or Eu.

10. A method of detecting a nucleoside phosphate comprising:

combining at least one nucleoside phosphate and a luminescent probe according to claim 1 in an aqueous medium; and detecting a decrease in luminescence at one or more selected wavelengths from the luminescence of the probe at the one or more selected wavelengths in the absence of the at least one nucleoside phosphate, indicating the presence of the at least one nucleoside phosphate.

11. The method of claim 10 wherein the at least one nucleoside phosphate is selected from the group consisting of nucleoside monophosphates, nucleoside diphosphates, nucleoside triphosphates, and combinations thereof.

12. The method of claim 10 wherein the at least one nucleoside phosphate is selected from the group consisting of adenosine phosphates, guanosine phosphates, cytosine phosphates, uridine phosphates, cyclic adenosine monophosphate (cyclic AMP), 6-methyluridine phosphate, 8-bromoguanosine phosphate, thymine phosphate, and combinations thereof.

13. The method of claim 10 wherein the luminescence is measured with excitation at 280 nm to 370 nm.

14. The method of claim 10 wherein the luminescence is detected at one or more wavelengths selected from the group consisting of wavelengths of 450 to 690 nm, wavelengths of 800 to 1200 nm, or wavelengths of 1500 to 1600 nm.

15. The luminescent probe of claim 1 wherein the chelator comprises a 1,4,7,10-tetraazacyclododecane-1,4,7,-triacetic acid-10-acetamide (DOTA) chelator.

16. The luminescent probe of claim 15 wherein Z represents a group of the Formula Z3:

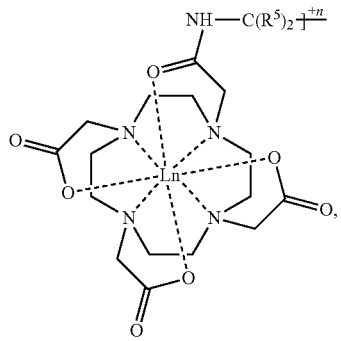

wherein each $R^5$ independently represent H.

17. The luminescent probe of claim 16 wherein:
each $R^1$ represents hydrogen or Z;
$R^3$ represents hydrogen;
n=0; and
Z represents a chelated luminescent Europium (Eu) complex, with the proviso that one $R^1$=Z.

18. The luminescent probe of claim 17 wherein each $R^5$ represents hydrogen.

19. The luminescent probe of claim 1 comprising a structure of the formula:

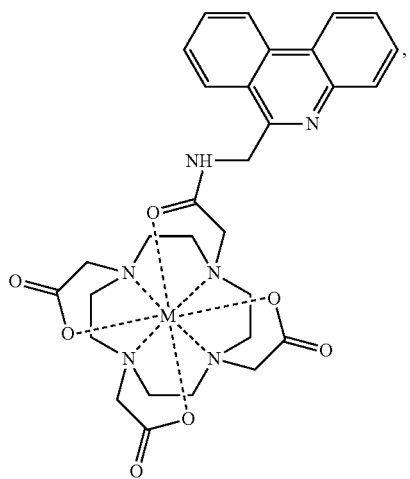

Formula III wherein M represents Tb or Eu.

20. A method of detecting a nucleoside phosphate comprising:
combining in an aqueous medium at least one nucleoside phosphate, a first luminescent probe, and a second luminescent probe;
detecting a decrease in luminescence at one or more selected wavelengths from the luminescence of at least one of the probes at the one or more selected wavelengths in the absence of the at least one nucleoside phosphate, indicating the presence of the at least one nucleoside phosphate;
wherein the first and second luminescent probes have a structure of the formula:

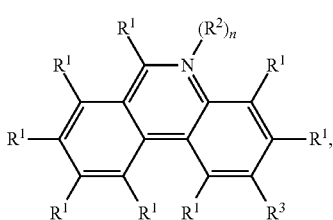

Formula I wherein:
each $R^1$ represents hydrogen, a C1-C10 hydrocarbon moiety, a halogen, or Z;
$R^2$ represents hydrogen or a C1-C10 hydrocarbon moiety;
$R^3$ represents hydrogen, a C1-C10 hydrocarbon moiety, or a halogen;
wherein for molecules in which one or more of $R^1$, $R^2$, and/or $R^3$ represents a C1-C10 hydrocarbon moiety, two or more of $R^1$, $R^2$, and $R^3$ may optionally be joined with one another to form one or more fused rings;
n=0 or 1; and
Z represents a chelated luminescent Lanthanide (Ln) complex attached to the phenanthridine with a —C($R^5$)$_2$NHC(O)CH$_2$-Lanthanide (Ln) complex linkage, wherein each $R^5$ independently represents hydrogen, with the proviso that one $R^1$=Z;
wherein the chelated Lanthanide complex of the first luminescent probe comprises a polyamino carboxamide chelated Lanthanide, wherein the polyamino carboxamide chelator is selected from the group consisting of a 1,4,7,10-tetraazacyclododecane-1,4,7,10-tetraacetamide (DOTAm) chelator and a diethylene triamine pentaacetamide (DTPAm) chelator; and
wherein the chelator of the second luminescent probe comprises a 1,4,7,10-tetraazacyclododecane-1,4,7,-triacetic acid-10-acetamide (DOTA) chelator.

* * * * *